(12) United States Patent
Siegal

(10) Patent No.: US 10,591,029 B2
(45) Date of Patent: Mar. 17, 2020

(54) APPARATUS FOR ADVANCEMENT ALONG A PREDETERMINED CURVED TRAJECTORY AND A METHOD FOR OPERATION THEREOF

(71) Applicant: Tzony Siegal, Shoeva (IL)

(72) Inventor: Tzony Siegal, Shoeva (IL)

( * ) Notice: Subject to any disclaimer, the term of this patent is extended or adjusted under 35 U.S.C. 154(b) by 623 days.

(21) Appl. No.: 15/118,899

(22) PCT Filed: Feb. 18, 2015

(86) PCT No.: PCT/IL2015/050186
§ 371 (c)(1),
(2) Date: Aug. 15, 2016

(87) PCT Pub. No.: WO2015/125140
PCT Pub. Date: Aug. 27, 2015

(65) Prior Publication Data
US 2016/0348769 A1 Dec. 1, 2016

(30) Foreign Application Priority Data
Feb. 20, 2014 (IL) .......................................... 231054

(51) Int. Cl.
*F16H 19/02* (2006.01)
*F16H 19/06* (2006.01)
(Continued)

(52) U.S. Cl.
CPC ......... *F16H 19/0636* (2013.01); *A61B 1/008* (2013.01); *A61B 17/00234* (2013.01);
(Continued)

(58) Field of Classification Search
CPC . A61B 1/0055; A61B 1/008; A61B 2017/003; A61B 2017/00314
See application file for complete search history.

(56) References Cited

U.S. PATENT DOCUMENTS 5,762,067 A * 6/1998 Dunham .............. A61B 1/0052
600/148
7,670,284 B2 3/2010 Padget et al.
(Continued)

FOREIGN PATENT DOCUMENTS

WO 2015/125140 A1 8/2015

OTHER PUBLICATIONS

International Search Report of PCT/IL2015/050186, dated May 18, 2015.
(Continued)

*Primary Examiner* — Andrew M Tecco
*Assistant Examiner* — Eyamindae C Jallow

(57) ABSTRACT

An apparatus for advancement along a predetermined curved trajectory, comprising: a conduit having a conduit distal end; an elongated member having a main axis, at least partially extending within said conduit and movable therein along its length, said elongated member comprising a segmented assembly formed of a plurality of segments hingedly connected with each other, each having an orientation axis perpendicular to the main axis; and a deflecting member extending along said main axis so as to have a first state with a first extension along at least a part of the segmented assembly including its most distal segment, and a second state with a second extension along said part of the segmented assembly, the second extension exceeding the first extension.

9 Claims, 17 Drawing Sheets

(51) Int. Cl.
  *A61B 1/008* (2006.01)
  *A61B 17/00* (2006.01)
  *F16C 1/02* (2006.01)
  *F16G 13/20* (2006.01)
  *F16H 19/04* (2006.01)

(52) U.S. Cl.
  CPC ............... *F16C 1/02* (2013.01); *F16G 13/20* (2013.01); *F16H 19/04* (2013.01); *A61B 2017/00314* (2013.01); *A61B 2017/00331* (2013.01); *A61B 2017/00336* (2013.01); *F16H 2019/069* (2013.01)

(56) References Cited

U.S. PATENT DOCUMENTS

| | | | | |
|---|---|---|---|---|
| 2006/0074383 | A1* | 4/2006 | Boulais | A61B 1/0052 604/95.04 |
| 2009/0054733 | A1* | 2/2009 | Marescaux | A61B 17/29 600/141 |
| 2009/0177041 | A1* | 7/2009 | Stefanchik | A61B 1/00073 600/146 |
| 2010/0076433 | A1* | 3/2010 | Taylor | A61B 18/1445 606/52 |
| 2011/0208211 | A1* | 8/2011 | Whitfield | A61B 17/1285 606/142 |
| 2011/0213363 | A1* | 9/2011 | Cunningham | A61B 18/1445 606/41 |
| 2012/0078243 | A1 | 3/2012 | Worrell et al. | |
| 2012/0078377 | A1 | 3/2012 | Gonzales et al. | |
| 2012/0109186 | A1* | 5/2012 | Parrott | A61B 17/29 606/206 |
| 2013/0123783 | A1* | 5/2013 | Marczyk | A61B 17/29 606/45 |
| 2013/0331825 | A1* | 12/2013 | Mitchell | A61B 17/320016 606/1 |
| 2013/0338647 | A1* | 12/2013 | Bacher | A61N 5/00 606/1 |
| 2014/0135685 | A1* | 5/2014 | Kabe | A61M 25/0138 604/95.04 |
| 2016/0022355 | A1* | 1/2016 | Sakaguchi | A61B 17/29 606/34 |

OTHER PUBLICATIONS

Written Opinion of the International Search Authority of PCT/IL2015/050186, dated May 18, 2015.

\* cited by examiner

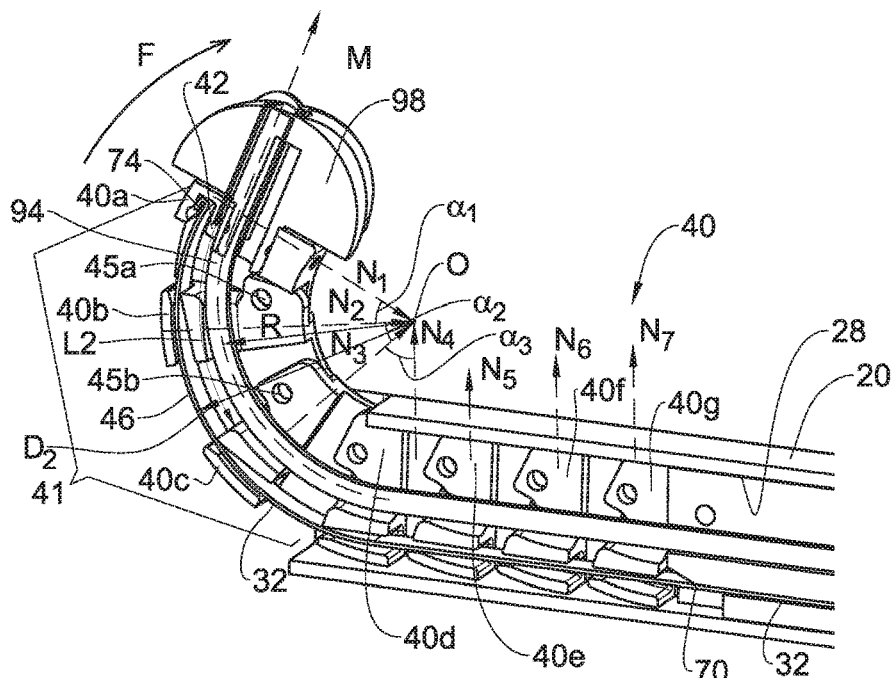
Fig. 2D
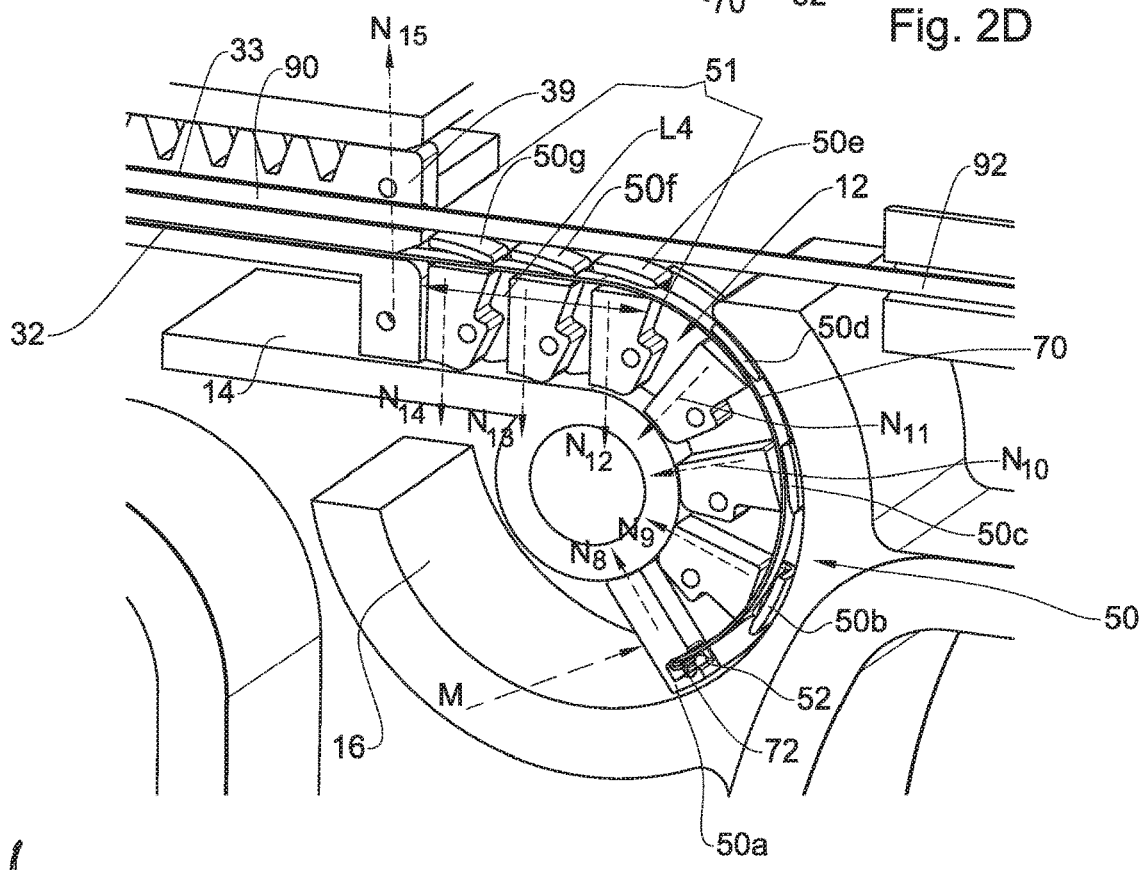
Fig. 2E
Fig. 2F

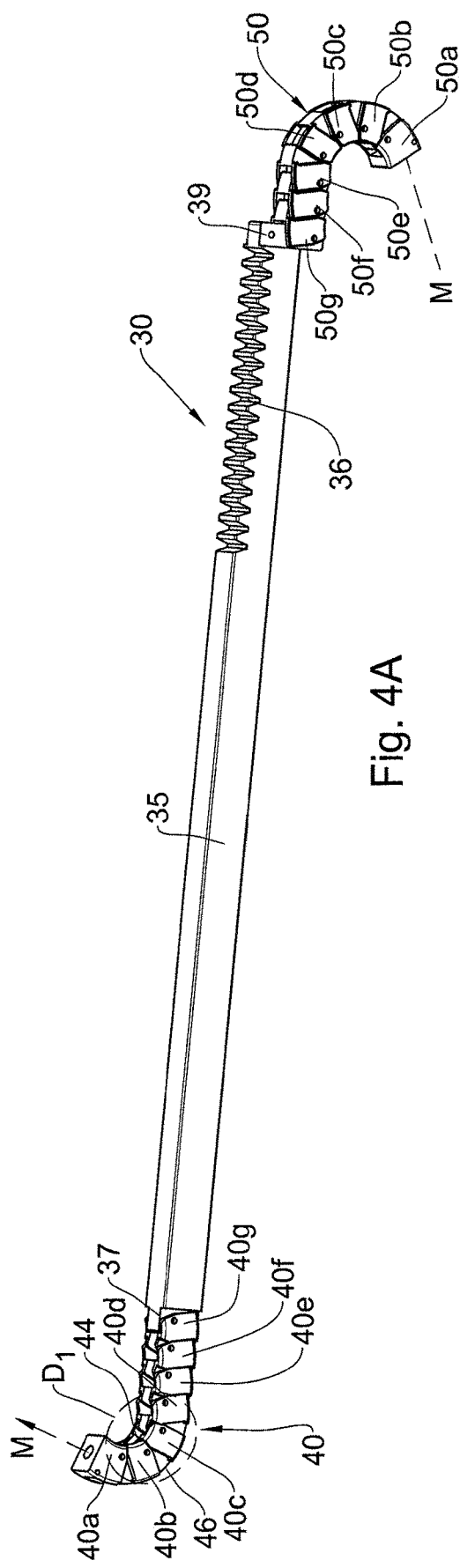
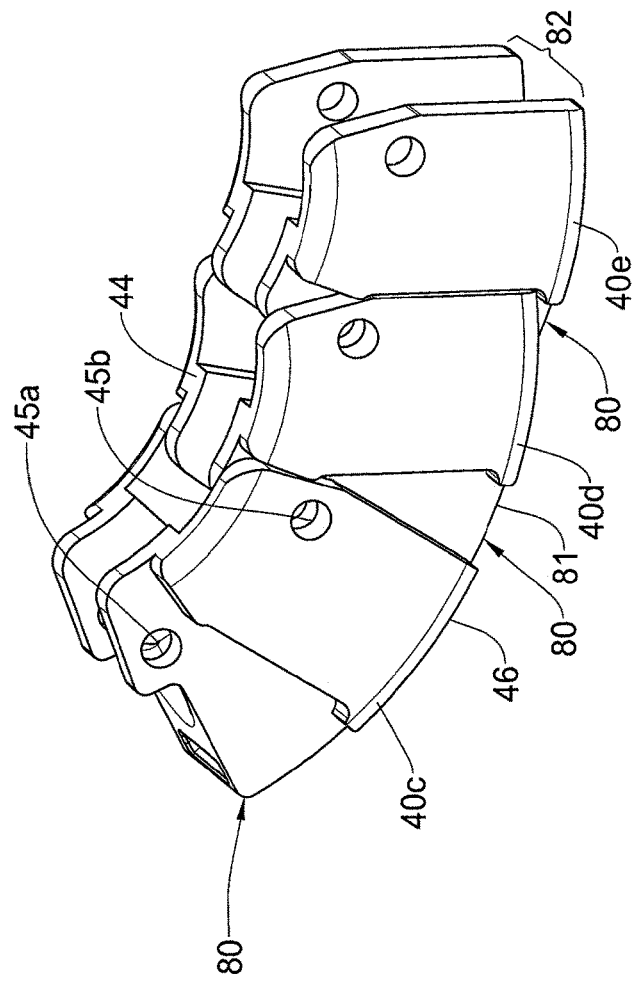
Fig. 4A
Fig. 4B

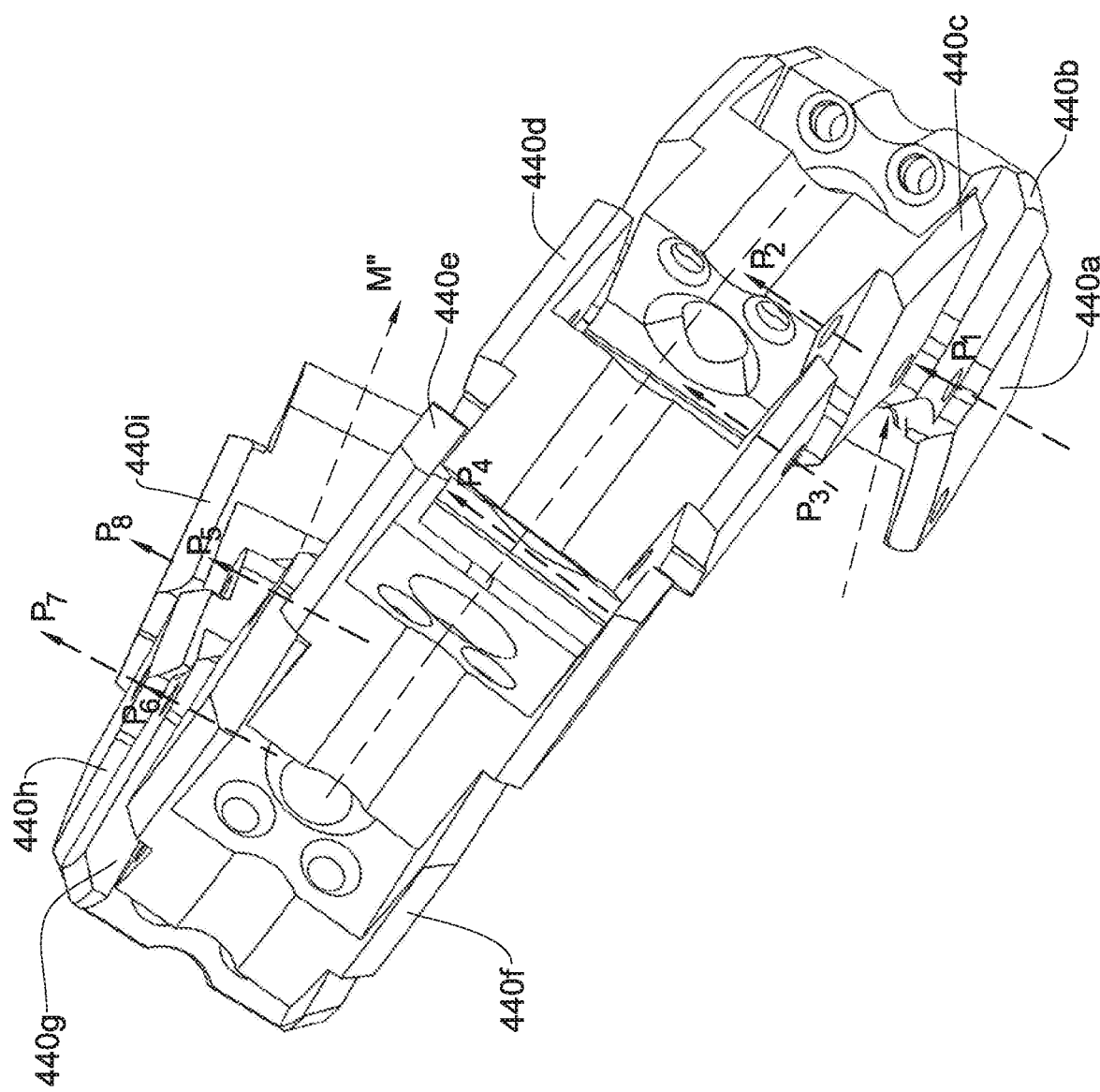

APPARATUS FOR ADVANCEMENT ALONG A PREDETERMINED CURVED TRAJECTORY AND A METHOD FOR OPERATION THEREOF

CROSS-REFERENCE TO RELATED APPLICATIONS

This application is a national phase filing under 35 U.S.C. 371 of International Application No. PCT/IL2015/050186, filed Feb. 18, 2015, which claims priority from Israeli Patent Application No. 231054, filed Feb. 20, 2014, the disclosures of which are hereby incorporated by reference in their entirety.

TECHNOLOGICAL FIELD

The presently disclosed subject matter is related to the field of apparatuses used for introduction into a structure, in particular, apparatuses made for advancement along a predetermined curved trajectory.

BACKGROUND

Apparatuses for introduction into a structure via an opening (e.g. a hole) have been known for many years, and are used for different applications. For example, these apparatuses are known as: drills which are used in mechanical engineering, catheters which are used in medical endoscopy, monitoring devices which are used for various monitoring purposes, etc. In some cases, there is a need to introduce an apparatus along a straight path, and at some later stage to change the path of the introduction to a predetermined curved trajectory in which the device should be stable and its path should be well defined.

GENERAL DESCRIPTION

The presently disclosed subject matter is related to an apparatus and a method for introduction into an object along a straight path and advancement therein along a predetermined curved trajectory. The apparatus and the method can be used for a wide variety of applications, for example: constituting a carrier for introducing an least one object into a structure; monitoring a particular location within a structure; forming a curved channel within or though a structure; clearing a path within a structure, e.g., by drilling; providing a curved anchoring member within a structure; forming a reinforcing member within a structure; cutting-out a sample of material from a structure; filling a region within a structure; and expanding a spacing between parts of a structure.

The term 'structure' refers hereinafter in the specification and the claims to any part or element known in the fields of medicine, mechanics, physics, engineering, etc. The structure can be for example, a human body; an animal body; and an inanimate object. The structure can be made, for example, of the following materials or combination thereof: concrete, wood, metal, plastics and soil, etc.

The dimensions of the apparatus and the structure of its parts can be chosen in accordance with the intended application to be performed.

According to a first aspect of the presently disclosed subject matter, there is provided an apparatus for advancement along a predetermined curved trajectory, comprising:

a. a conduit having a conduit distal end;

b. an elongated member having a main axis, at least partially extending within said conduit and movable therein along its length. The elongated member comprises a segmented assembly formed of a plurality of segments hingedly connected with each other, each having an orientation axis perpendicular to the main axis; and c. a deflecting member extending along said main axis so as to have a first state with a first extension along at least a part of the segmented assembly including its most distal segment, and a second state with a second extension along said part of the segmented assembly, the second extension exceeding the first extension.

The deflecting member has a distal end mechanically associated at least with said most distal segment of the segmented assembly so as to allow the distal end to exert a pushing force on at least the most distal segment at least when the deflecting member changes its state from the first state to the second state. The segmented assembly is configured to change its configuration, at least when the pushing force is exerted, from a straight configuration associated with the first state of the deflecting member, in which all the segments have their orientation axes parallel to each other, into a curved configuration associated with the second state of the deflecting member, in which at least the part of the segmented assembly extends beyond the conduit distal end and the corresponding segments of said part change their orientation with respect to each other by means of their hinges so that the orientation axes of the corresponding segments form an angle therebetween, and so that the part of the assembly is rendered a curved shape.

According to a second aspect of the presently disclosed subject matter, there is provided an apparatus for advancement along a predetermined curved trajectory, comprising:

a. a conduit having a conduit distal end;

b. an elongated member having a main axis, at least partially extending within the conduit and movable therein along its length. The elongated member comprises a segmented assembly formed of a plurality of segments hingedly connected with each other, each having an orientation axis perpendicular to the main axis; and c. a deflecting member extending along the conduit and configured to change configuration of the segmented assembly from a straight configuration in which all the segments have their orientation axes parallel to each other, into a curved configuration, in which at least a part of the segmented assembly including its most distal segment extends beyond the conduit distal end and the corresponding segments of said part change their orientation with respect to each other by means of their hinges so that the orientation axes of the corresponding segments form an angle therebetween, and so that the part of the assembly is rendered a curved shape.

The segmented assembly when in its curved configuration has a concave side and a convex side. At least in a majority of the segments, each pair of adjacent segments has stabilizing portions closer to the convex side than the concave side and that are other than the hinged connection therebetween. The stabilizing portions are configured to engage each other in both the straight and the curved configurations of the segmented assembly so as to resist torsion of the adjacent segments with respect to each other.

According to a third aspect of the presently disclosed subject matter, there is provided an apparatus for advancement along a predetermined curved trajectory, comprising:

a. a conduit having a conduit distal end;

b. an elongated member, having a main axis, at least partially extending within the conduit and movable therein along its length. The elongated member comprises a segmented assembly formed of a plurality of segments hingedly connected with each other, each having an orientation axis perpendicular to the main axis; and c. a deflecting member extending along the conduit and configured to change configuration of the segmented assembly from a straight configuration in which all the segments have their orientation axes parallel to each other, into a curved configuration, in which at least a part of the segmented assembly including its most distal segment extends beyond the conduit distal end and the corresponding segments of said part change their orientation with respect to each other by means of their hinges so that the orientation axes of the latter segments form an angle therebetween, and so that the part of the assembly is rendered a curved shape.

The segmented assembly when in its curved configuration has a concave side and a convex side. The hinges are disposed closer to the concave side than the deflecting member.

In the first aspect of the apparatus, the segmented assembly when in its curved configuration can have a concave side and a convex side. In the first and the third aspects of the apparatus, at least in a majority of the segments, each pair of adjacent segments can have stabilizing portions which are closer to the convex side than the concave side and that are other than the hinged connection therebetween. The stabilizing portions can be configured to engage each other in both the straight and the curved configurations of the segmented assembly so as to resist torsion of the adjacent segments with respect to each other.

In the first and the second aspects of the apparatus, the hinges can be disposed closer to the concave side than the deflecting member.

Any one or more of the following features, designs and configurations can be incorporated in the apparatus according to the presently disclosed subject matter, independently or in combination thereof:

In the straight configuration, the segments associated with the part of the assembly can be restricted by an internal wall of the conduit to assume their parallel orientation with respect to each other.

The distal end of the deflecting member can further be mechanically associated with the most distal segment so as to allow the most distal segment to exert a pushing force on the distal end at least when the part of the segmented assembly is introduced into the conduit via the conduit distal end and the segmented assembly changes its configuration from the curved to the straight configuration, thereby changing the state of the deflecting member from the second state to the first state.

The apparatus can further comprise a moving mechanism configured for applying a pushing force on the elongated member for moving the elongated member along the conduit and causing the part of the segmented assembly to extend beyond the conduit distal end and to be introduced into the conduit via the conduit distal end.

The apparatus can further comprise an actuator being mechanically associated with the deflecting member and configured for moving the deflecting member along said main axis and changing its state between the first and the second states.

The moving mechanism can be mechanically associated with the actuator, so that operation of the moving mechanism to move the elongated member along the conduit entails operation of the actuator to move the deflecting member in the same direction, thereby assisting in the movement of the elongated member in that direction.

The ability of both the deflecting member and the moving mechanism to apply pushing forces at the same direction allows effectively advancing the segment assembly into the structure. The fact that the direction of movement of the deflecting member is similar to that of the elongated member allows the deflecting member to assist in the advancement of the elongated member into the structure and to improve this advancement.

The elongated member can further comprise an additional segmented assembly and a movable member having a first end to which the segmented assembly is connected and a second end to which the additional segmented assembly is connected.

The additional segmented assembly can be formed of a plurality of additional segments hingedly connected with each other, each having an orientation axis perpendicular to the main axis. The deflecting member extending along said main axis so as to have an additional first state with an additional first extension along at least a part of the additional segmented assembly including its segment being most distal to the segmented assembly, and an additional second state with an additional second extension along said part of the additional segmented assembly. The additional first extension is exceeding the additional second extension. The deflecting member can have a proximal end mechanically associated at least with said most proximal segment of said additional segmented assembly so as to allow said most proximal segment to exert a pushing force on the proximal end of the deflecting member, at least when the deflecting member is changing its state from the additional first state to the additional second state. The additional segmented assembly can be configured to change its configuration, at least when said pushing force on the said proximal end is exerted, from an additional curved configuration associated with said additional first state of the deflecting member, in which all the additional segments are disposed in orientation with respect to each other by means of their hinges so that the orientation axes of the corresponding segments form an angle therebetween, into an additional straight configuration associated with said additional second state of the deflecting member, in which the segments of the part of the additional segmented assembly have their orientation axes parallel to each other.

The number of the additional segments can be identical to the number of the segments of the segmented assembly.

In the first state of the deflecting member it can assume its additional first state and in the second state of the deflecting member it can assume its additional second state.

The curved shape can be similar or identical to the additional curved shape.

The actuator can be constituted by the segmented assembly and by the additional segmented assembly so that: operation of the moving mechanism to move the elongated member along the conduit to cause said segmented assembly to extend from the conduit distal end, entails the part of the additional segmented assembly to change its configuration from the additional curved configuration to the additional straight configuration, which entails the most proximal segment of the additional segmented assembly to exert a pushing force of the proximal end on the deflecting member, causing it to move in the same direction and to change its state from the first to the second state, thereby changing the configuration of the segmented assembly from the straight to the curved configuration; and operation of the moving mechanism to move the elongated member along the conduit to cause said segmented assembly to be introduced into the conduit via the conduit distal end, entails the segmented assembly to change its configuration from the curved configuration to the straight configuration, which entails the most distal segment to exert a pushing force on the distal end of the deflecting member, causing it to move in the same direction and to change its state from the additional second state to the additional first state, thereby changing the configuration of the additional segmented assembly from the additional straight configuration to the additional curved configuration.

The curved channel can have a straight portion extending along the conduit for housing the additional segmented assembly in its additional straight configuration and a curved portion for housing the part of the additional segmented assembly therein in the additional curved configuration of the additional segmented assembly. The additional segmented assembly can be movable within the curved channel between its additional straight configuration and additional curved configuration.

The moving mechanism can comprise a rack and pinion gear in which the pinion is a circular gear and the rack is a linear gear formed along the elongated member.

The stabilizing portions can be constituted by a projecting portion of one segment and a recessed portion of its adjacent segment, configured to receive the projecting portion.

The hinges can be disposed in proximity to the concave side and the deflecting member can be disposed in proximity to the convex side.

The curved shape can be an arc characterized by a center of curvature O facing the concave side and a radius R defined between the main axis and the center of curvature O. The hinges of the part of the segmented assembly can be equally spaced from the center of curvature O to a first distance D1 and the deflecting member extending along a first channel formed in the elongated member. The first channel can be spaced from the center of curvature O to a second distance D2 and the following condition is fulfilled: D1<R<D2.

Each segment of at least a majority of said segments can comprise: an inner segment face constituting a part of the concave side; an outer segment face opposite thereto, constituting a part of the convex side; first and second opposite outer wings, constituting at least a part of the recessed portion, respectively extending between the inner segment face and the outer segment face therebetween; and first and second opposite inner wings, constituting at least a part of the projecting portion, respectively extending between the inner segment face and the outer segment face. The first and second inner wings of one segment can be received and hingedly movable within the recessed portion formed between the first and second outer wings of its adjacent segment, thereby forming the segmented assembly and allowing the segmented assembly to change its configuration.

The connection between two adjacent segments can be such that the first outer wing of one segment is pivotally connected to the first inner wing of its adjacent segment and the second outer wing of said one segment is pivotally connected to the first inner wing of the adjacent segment.

Each of the first and the second outer wings can comprise: a first front contact surface; a second front contact surface; a first rear contact surface and a second rear contact surface, so that in the straight configuration, the second rear contact surfaces of one segment contact the second front contact surfaces of its adjacent segment, thereby providing a contact surface between the two adjacent segments in addition to the hinges therebetween, and in the curved configuration, the first front contact surfaces of one segment contact the first rear contact surfaces of its adjacent segment, thereby delimiting the deflection of these segments with respect to each other to a predefined extent and transferring the pushing force from the most distal segment to at least one of its successive segments for causing them to form an angle between orientation axes of the adjacent segments.

Exertion of the pushing force by the moving mechanism can transfer this force between two segments disposed in the straight orientation with respect to each other by the contact between the second front contact surfaces of one segment with the second rear contact surfaces of its adjacent segment, in addition to the hinges therebetween, and between two segments with an angle between their orientation axes by contact between the first front contact surfaces of one segment with the first rear contact surfaces of its adjacent segment, in addition to the hinges therebetween.

The deflecting member can be selected from a group comprising: an elongated metal strip, an elongated bendable rod, a roller chain and a cardan shaft.

Each of the segments can include a second channel configured to allow passage of a working tool through the elongated member.

The apparatus can further comprise the above working tool comprising a shaft received within the second channels of the segments and a tip mountable to a distal end of the shaft in proximity to the most distal segment.

The shaft can be rotatable.

During initiation of a drilling operation by the apparatus of the presently disclosed subject matter and the change of configuration from the straight to the curved configuration, the following forces can be exerted simultaneously:

A pushing force is exerted by the operator on the entire apparatus in the direction of drilling;

A pushing force is exerted by the moving mechanism on the elongated member along the axis of drilling; and A pushing force is exerted by the deflecting member on the most distal segment, having a vector component along the axis of drilling.

The fact that the above three pushing forces are exerted substantially and at least partially in the same direction at least during initiation of the drilling operation, an effective drilling of the structure is obtained. When these forces are exerted, a superposition of them can provide an intensified and effective drilling within the object.

According to a fourth aspect of the presently disclosed subject matter, there is provided a method for operating an apparatus for advancement along a predetermined curved trajectory. The method comprises steps of:

a. obtaining said apparatus, comprising: a conduit having a conduit distal end; an elongated member having a main axis, at least partially extending within said conduit and movable therein along its length. The elongated member comprises a segmented assembly formed of a plurality of segments hingedly connected with each other, each having an orientation axis perpendicular to the main axis; and a deflecting member extending along said main axis so as to have a first state with a first extension along at least a part of the segmented assembly including its most distal segment, and a second state with a second extension along said part of the segmented assembly, the second extension exceeding the first extension; said deflecting member having a distal end mechanically associated at least with said most distal segment of said segmented assembly;

b. moving the elongated member along the conduit so as to cause at least said part of the segmented assembly to extend beyond the conduit distal end;

c. changing the state of the deflecting member from the first to the second state, thereby causing the distal end of the deflecting member to exert a pushing force on at least the most distal segment; and d. causing the segmented assembly, at least by way of said pushing force, to change its configuration from a straight configuration associated with said first state of the deflecting member, in which all the segments have their orientation axes parallel to each other, into a curved configuration associated with said second state of the deflecting member, in which at least said part of the segmented assembly extends beyond said conduit distal end and the corresponding segments of said part change their orientation with respect to each other by means of their hinges so that the orientation axes of the corresponding segments, thereby rendering said part of the segmented assembly a curved shape.

The step (b) can trigger the step (c) which can trigger the step (d).

The step (d) can be performed by moving the deflecting member by an actuator along the conduit in a direction of movement which is similar to the direction of movement of the elongated member.

The method can further comprise a step of moving the elongated member along the conduit so as to cause at least said part of the segmented assembly to be introduced into the conduit distal end, thereby causing the most distal segment to exert a pushing force on the distal end at least when the part of the segmented assembly, changing the state of the deflecting member from the second state to the first state and allowing the segmented assembly to change its configuration from the curved to the straight configuration.

The movement of the elongated member can be performed by operating a moving mechanism which applies a pushing force on the elongated member in the respective direction of movement of the elongated member.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 2D is an enlarged view of section $B_1$ of FIG. 2C;

FIG. 2E is an enlarged view of section $B_2$ of FIG. 2C;

FIG. 2F is a side view of the deflecting member of FIG. 2C;

FIG. 4A is a side view of an elongated member of FIG. 2B with other parts of the apparatus being removed;

FIG. 4B is an enlarged view of three segments from section $D_1$ of FIG. 4A;

FIG. 8B is another view of the segmented assembly of FIG. 8A; and

DETAILED DESCRIPTION OF EMBODIMENTS

Figure 1A:
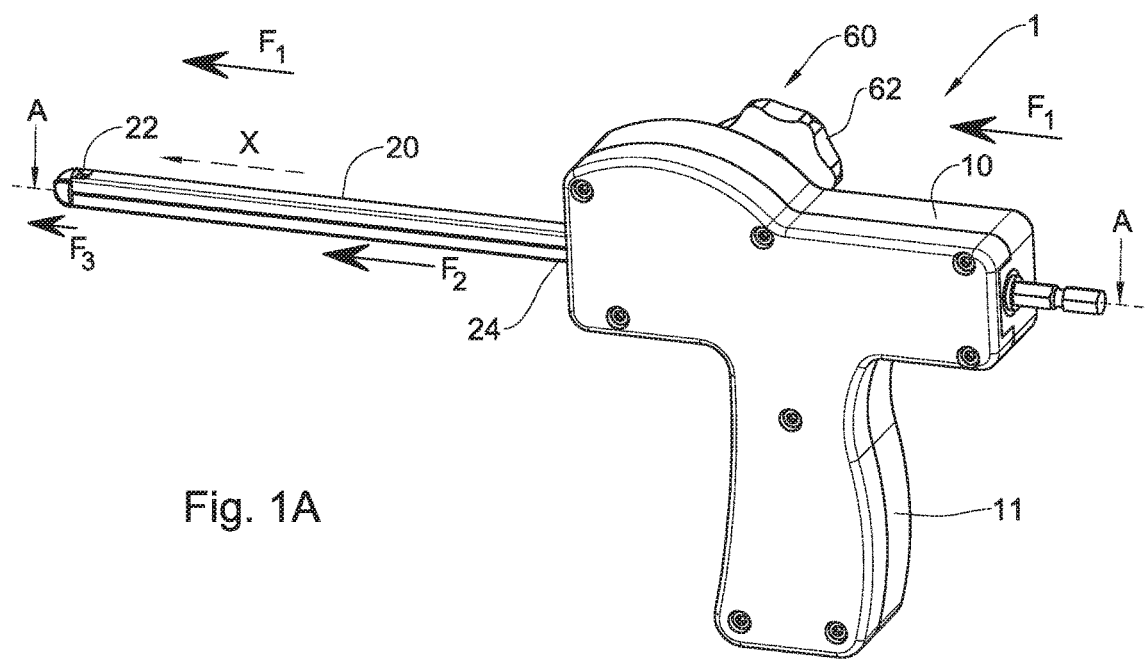
FIG. 1A is a side view of an apparatus, in accordance with one example of the presently disclosed subject matter, with its segmented assembly in its straight configuration.
Figure 1B:
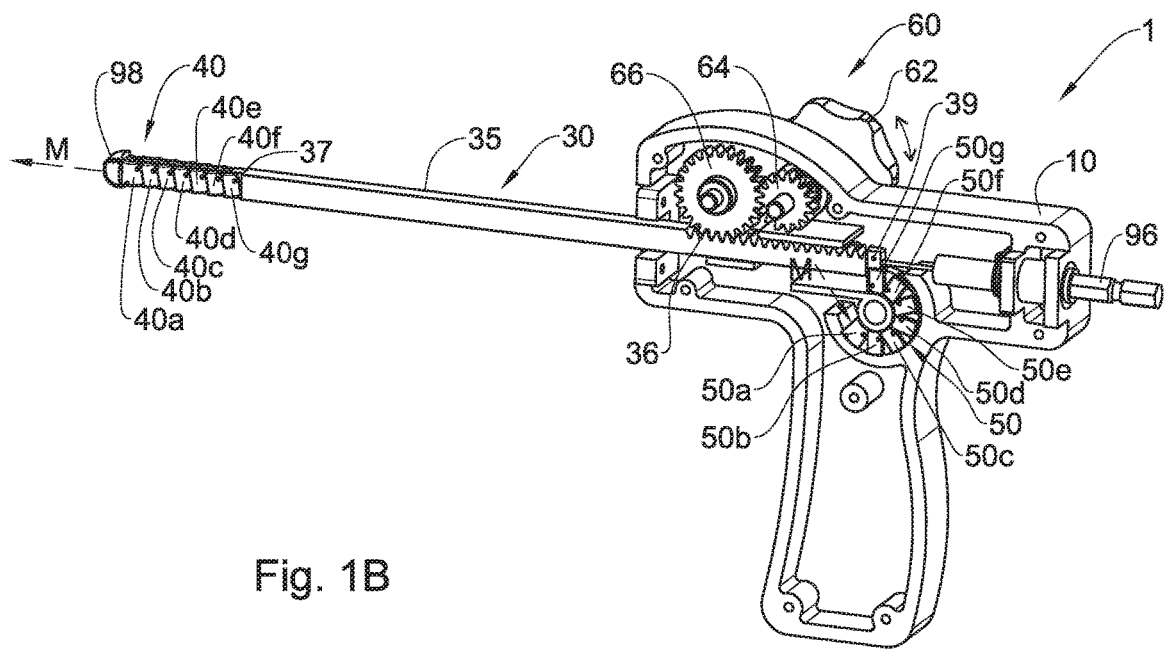
FIG. 1B is the apparatus of FIG. 1A with a part of its housing and its conduit being removed.
Figure 1C:
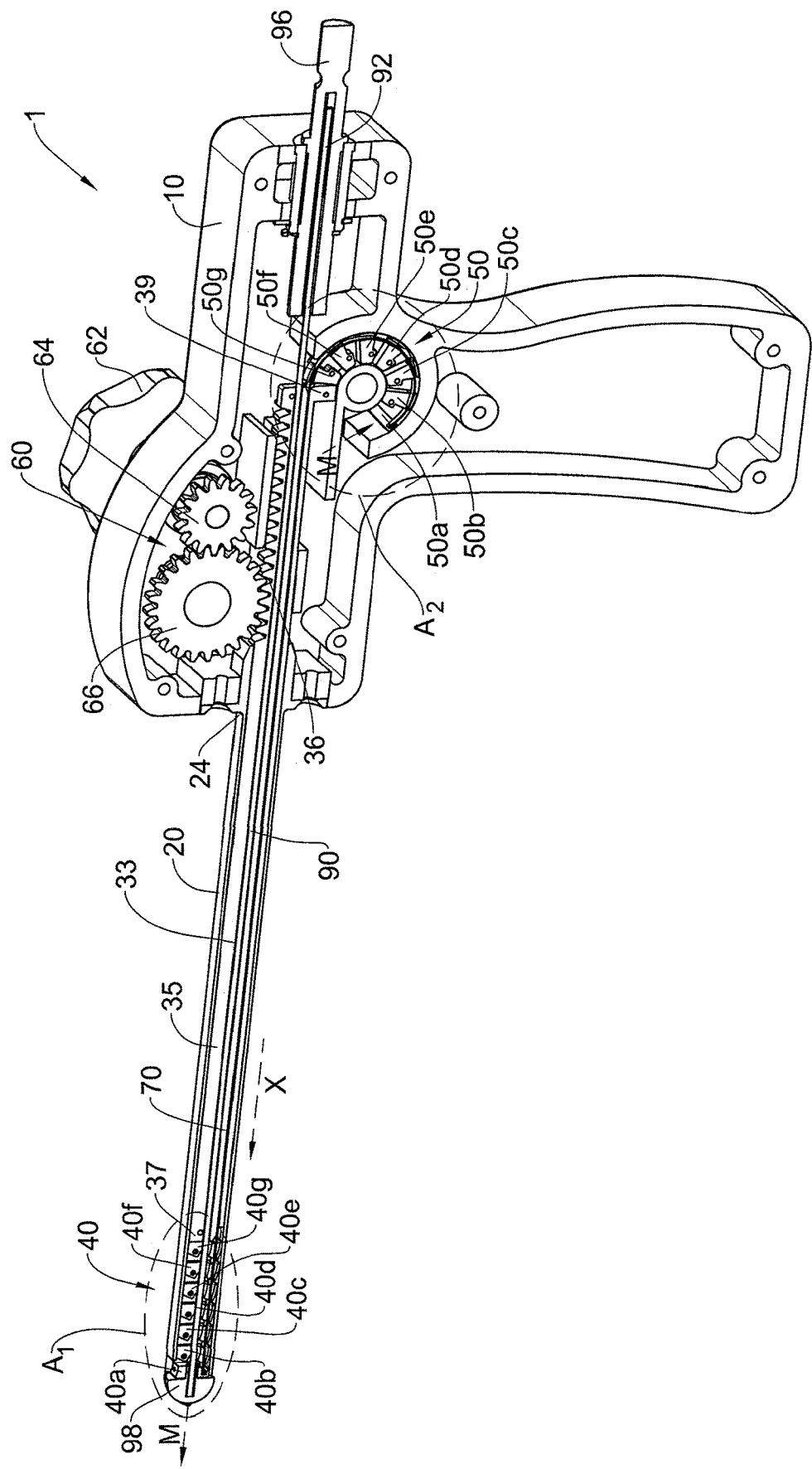
FIG. 1C is a cross-section view along line A-A in FIG. 1A.

Reference is first made to FIGS. 1A to 1F, 2A to 2F and 3A to 3F in order to describe an apparatus 1 and its manner of operation, in accordance with one example of the presently disclosed subject matter.

According to the examples of the above figures, the apparatus 1 is a drill which is configured for advancement along a predetermined curved trajectory. It is appreciated that the apparatus of the presently disclosed subject matter according to its different aspects can have applications other than drilling, and drilling is only one of them.

The apparatus 1 comprises the following components: a housing 10, a conduit 20 extending from the housing 10, an elongated member 30 with a segmented assembly 40, a moving mechanism 60 and a deflecting member 70. In general, the operation of the apparatus 1 is such that actuation of the moving mechanism 60 causes the segmented assembly 40 to extend outside from the conduit 20 automatically entailing deflection of the extending part of the segmented assembly 40 by the deflecting member 70 to a predetermined stabilized curved shape. In addition, actuation of the moving mechanism 60 to cause the segmented assembly 40 to be introduced into the conduit 20 automatically entails the introduced part of the segmented assembly 40 to be straightened within the conduit 20.

FIGS. 1A to 1F illustrate the apparatus 1 with the segmented assembly fully disposed within the conduit 20. FIGS. 2A to 2F illustrate the apparatus 1 with a part of the segmented assembly 40 extending out of the conduit 20 and having a curved shape. FIGS. 3A to 3F illustrate the apparatus 1 with the segmented assembly 40 fully extending out of the conduit 20 and having a respective curved shape.

Below is a detailed explanation regarding the structure of the apparatus 1 and its manner of operation.

The housing 10 has a handle 11 shaped so as to fit a hand of an operator of the apparatus 1. The conduit 20 has a conduit distal end 22 with an opening and a conduit proximal end 24 connected to the housing 10. The conduit distal end 22 and the conduit proximal end 24 extend along an axis X.

When the operator holds the apparatus 1 at the handle 11, the conduit distal end 22 can be introduced into an aperture of a structure to be treated. If the aperture does not exist, the conduit distal end 22 can be disposed by the operator in proximity to the structure, at a location in which the aperture should be created by the apparatus 1.

The elongated member 30 (shown in a detailed manner in FIG. 4A) extends along the conduit 20 and within the housing 10. The elongated member 30 comprises a movable member 35, the segmented assembly 40 and an additional segmented assembly 50. The movable member 35 has a first end 37 to which the segmented assembly 40 is pivotally connected and a second end 39 to which the additional segmented assembly 50 is pivotally connected. The elongated member 30 has a main axis M defined as an axis extending at the middle of the elongated member 30 along its entire length.

The housing 10 has a curved channel 12 in which the additional segmented assembly 50 is seated and movable. The curved channel 12 has a straight portion 14 and a curved portion 16. The curved channel 12 is structured so that the part of the additional segmented assembly 50 which is received within the straight portion 14, is forced to assume a straight shape, and the part of the additional segmented assembly 50 which is received within the curved portion 16 is forced to assume a curved shape.

The moving mechanism 60 is configured to move the elongated member 30 along the axis X within the conduit 20, for causing a part of the segmented assembly 40 or the entire segmented assembly 40 to extend beyond the conduit distal end 22, and for causing the segmented assembly 40 (as shown, for example, in FIGS. 2A and 3A) to be introduced into the conduit 20 via the conduit distal end 22. Movement of the elongated member 30 also causes the additional segmented assembly 50 to move within the curved channel 12 along the axis M in a respective manner. The structure and operation of the moving mechanism 60 is detailed below.

After introduction of the conduit 20 into the structure to be treated, and upon the operator's decision, the moving mechanism 60 is actuated for causing the segmented assembly 40 to extend beyond the conduit distal end 22 while its shape is curved proportionally to its extension beyond the conduit distal end 22.

The moving mechanism 60 includes a rack and pinion gear constituted by the following components: a rotatable handle 62 mounted to a small circular gear 64 which in turn rotates a large circular gear 66. The large circular gear 66 is seated on a linear gear 36 formed in the movable member 35. Clockwise rotation of the handle 62 (when seen from the front face of the handle 62), rotates the small circular gear 64 in the same direction, thereby rotating the large circular gear 66 in the anti-clockwise direction, which in turn applies a pushing force on the movable member 35. This pushing force causes the segmented assembly 40 to extend beyond the conduit distal end 22. Anti-clockwise rotation of the handle 62 causes the segmented assembly 40 to be introduced in the conduit 20 via the conduit distal end 22.

The moving mechanism 60 can be structured so the when each segment of the segmented assembly 40 escapes from the conduit distal end 22, an audible indication of a "click" is provided to the operator of the apparatus 1. This indication allows the operator to receive information regarding the advancement and the curvature of the part segmented assembly 40 that extends from the conduit 20 and is disposed within the structure. In other words, by hearing each "click", the operator can know what is the length of the part of the segmented assembly that has escaped from the conduit 20, and respectively can know what is the extent of the curvature of this part.

The segmented assembly 40 is formed of seven segments 40a, 40b, 40c, 40d, 40e, 40f and 40g (shown in FIGS. 1B, 1C, 1D, 2D and 3D) that are pivotally connected to each other by pivots. For example, the segments 40a and 40b and connected therebetween by a pivot 45a, and the segments 40b and 40c and pivotally connected therebetween by a pivot 45b. As shown in FIGS. 1D, 2D and 3D, each of the segments 40a, 40b, 40c, 40d, 40e, 40f and 40g has a respective orientation axis $N_1$, $N_2$, $N_3$, $N_4$, $N_5$, $N_6$ and $N_7$, each being perpendicular to the main axis M.

The additional segmented assembly 50 is formed of seven segments 50a, 50b, 50c, 50d, 50e, 50f and 50g (shown in FIGS. 1B, 1C, 1E, 2E and 3E) that are also pivotally connected to each other by pivots. As shown in FIGS. 1E, 2E and 3E, each of the segments 50a, 50b, 50c, 50d, 50e, 50f and 50g has a respective orientation axis $N_8$, $N_9$, $N_{10}$, $N_{11}$, $N_{12}$, $N_{13}$ and $N_{14}$, each being perpendicular to the main axis M. Detailed description of the structure of the above segments is provided below with reference to FIGS. 4B to 4E.

The elongated member 30 has a first channel 32 extending along the main axis M between the most proximal segment 50a of the additional segmented assembly 50 and the most distal segment 40a of the segmented assembly 40 for accommodating the deflecting member 70 therein. According to the present example, the deflecting member 70 is an elongated flexible and rigid strip clearly shown in FIGS. 1F, 2F and 3F in its different states.

The deflecting member 70 has a proximal end 72 and a distal end 74. The proximal end 72 is seated within a proximal recess 52 formed within the most proximal segment 50a and the distal end 74 is seated within a distal recess 42 formed within the most distal segment 40a. The proximal and the distal ends 72 and 74 are not bounded or connected to the segments 50a and 40a so that the deflecting member 70 has a freedom of slight movement within the first channel 32 upon operation of the moving mechanism 60.

The segmented assembly 40 and the additional segmented assembly 50 constitute an actuator, the role of which is to move the deflecting member 70 within the first channel 32 and to change the shape of the segmented assembly 40 and of the additional segmented assembly 50.

As generally mentioned above, the role of the deflecting member 70 is to cause the part of the segmented assembly that extends from the conduit distal end 22 to be maximally deflected from a straight to a predetermined curved shape, and to straighten the part of the segmented assembly that is introduced into the conduit 20 via the conduit distal end 22.

In general, when the moving mechanism 60 applies a pushing force on the elongated member 30 so as to cause a part of the segmented assembly 40 to extend beyond the distal end 22, the additional segmented assembly 50 is also drawn in the same direction. In particular, a similar part of the additional segmented assembly is received within the straight portion 14. This causes respective additional segments to pivotally approach each other, thereby shortening the length of a respective part of the first channel 32 by an extension Z (not shown) and causing the most proximal segment 50a to apply a pushing force on the proximal end 72 of the deflecting member 70. This pushing force causes the deflecting member 70 to move within the first channel 32 and to apply a pushing force on the most distal segment 40a. The extension Z is a sum of three extensions $Z_1$, $Z_2$ and $Z_3$ ($Z=Z_1+Z_2+Z_3$), which are shown in FIG. 1E. At the same time, it can be seen that not only that a part 41 extends beyond the conduit distal end 22, but also that pivotal rotation of the respective segments of the part 41 is performed due to a pushing force exerted by the distal end 74 of the deflecting member 70 on the most distal segment 40a. The ability of the respective segments of the part 41 to be pivotally rotated with respect to each other, allows increasing the respective length of the first channel 32 within the part 41 by the extension Z, thereby allowing the moving deflecting member 70 to be received within the longer portion of the first channel 32 while applying the pushing force on the most distal segment 40a. As a result of the operation of the moving mechanism 60, the part 41 extends beyond the conduit distal end, while a curved shape thereof is formed.

In order to explain in a detailed manner the operation of the apparatus 1 and the deflecting member 70 therein, reference is now made specifically to FIGS. 1D, 1E, 2D and 2E.

FIGS. 1D and 1E illustrate an initial position of the elongated member 30, and FIGS. 2D and 2E show an advanced position of the elongated member 30 provided as a result of a number of clockwise rotations of the handle 62.

As shown in FIG. 1D, the entire segmented assembly 40 is located within the conduit 20 and the segmented assembly 40 is in its straight configuration, in which all the segments 40a-40g of the segmented assembly 40 have their orientation axes $N_1$-$N_7$ parallel to each other. In this configuration, the segmented assembly 40 is restricted by an internal wall 28 of the conduit 20 to assume the parallel orientation between the axes $N_1$-$N_7$ of the segments 40a-40g.

In FIG. 2D, the segmented assembly 40 is in its curved configuration in which the part 41 of the segmented assembly 40 extends from the conduit distal end 22. The part 41 is constituted by the segments 40a, 40b and 4c. In the curved configuration, the segments 40a, 40b, 40c and 40d are pivotally rotated with respect to each other so that the orientation axes $N_1$, $N_2$, $N_3$ and $N_4$ form angles $\alpha_1$, $\alpha_2$ and $\alpha_3$ therebetween respectively, so that the part 41 is rendered a curved shape.

In FIG. 1E, the additional segmented assembly 50 is in its curved configuration in which all the additional segments 50a-50g are disposed in orientation with respect to each other by means of their pivots so that the orientation axes $N_8$-$N_{15}$ of the corresponding segments and the proximal end 39 form an angle therebetween, so that the entire additional segmented assembly 50 is rendered a curved shape. In this position, the entire additional segmented assembly 50 is located within the curved portion 16.

In FIG. 2E, a part 51 of the additional segmented assembly 50 is received within the straight portion 14. The part 51 is constituted by the segments 50e, 50f and 50g. According to this figure, the additional segmented assembly 50 is disposed in its additional curved configuration. In this configuration, the segments 50a, 50b and 50c and the proximal end 39 have their orientation axes $N_{12}$-$N_{15}$ parallel to each other.

The part 41 in FIG. 1D has a length being substantially similar to the length of the part 51 in FIG. 2E, and the part 41 in FIG. 2D has a length being similar to that of part 51 in FIG. 1E. In order to cause the part 41 to extend beyond the conduit distal end 22 and the part 51 to be received in the straight portion 14, the elongated member 30 was moved by the moving mechanism 60 to the respective extent along the axis X.

In FIG. 1D, the deflecting member 70 is disposed within the part 41 along a portion of the first channel 32 in its first state along a first extension $L_1$, and in FIG. 2D, the deflecting member 70 is disposed within the part 41 along a portion of the first channel 32 in its second state along a second extension $L_2$. It can be easily seen from the drawings that $L_2$ is greater than $L_1$. On the other hand, in FIG. 1E, the deflecting member 70 is disposed within the part 51 in its additional first state along a portion of the first channel 32 to an additional first extension $L_3$, and in FIG. 2E, the deflecting member 70 is disposed within the part 51 in its additional second state along a portion of the first channel 32 to an additional second extension $L_4$. It can be easily seen from the drawings that $L_3$ is greater than $L_4$.

When the elongated member 30 is moved by the moving mechanism 60 from the position of FIG. 1D to the position of FIG. 2D, the part 51 is drawn into the straight portion 14. This movement causes the following: the additional segment 50g is pivotally rotated toward the second end 39, the additional segment 50f is pivotally rotated toward the additional segment 50g and the additional segment 50e is pivotally rotated toward the additional segment 50f. When this takes place, the length of the first channel 32 within the part 51 is reduced, and thereby the length of the additional first extension $L_3$ is reduced by an extension Z (not shown) to the additional second extension $L_4$, so that the following equation is fulfilled: $L_3-Z=L_4$. At the same time, the part 41 is drawn from the conduit 30 to extend beyond the conduit distal end 32, allowing the segments 40a to pivotally rotate with respect to the segment 40b, the segment 40b to pivotally rotate with respect to the segment 40c, and the segment 40c to pivotally rotate with respect to the segment 40d. In view of the shortening in the length of the additional first extension $L_3$, the additional segment 50a exerts a pushing force on the proximal end 72. This pushing force causes the deflecting member 70 to move within the first channel 32 along the extension Z, which causes the distal end 74 of the deflecting member 70 to exert a pushing force of the segment 40a. The pushing force applied on the segment 40a, causes the following: the segment 40a is pivotally rotated with respect to the segment 40b, the segment 40b is pivotally rotated with respect to the segment 40c, and the segment 40c is pivotally rotated with respect to the segment 40d. Due to these rotations the first extension $L_1$ is increased by the extension Z to the second extension $L_2$, so that $L_1+Z=L_2$.

Figure 1D:
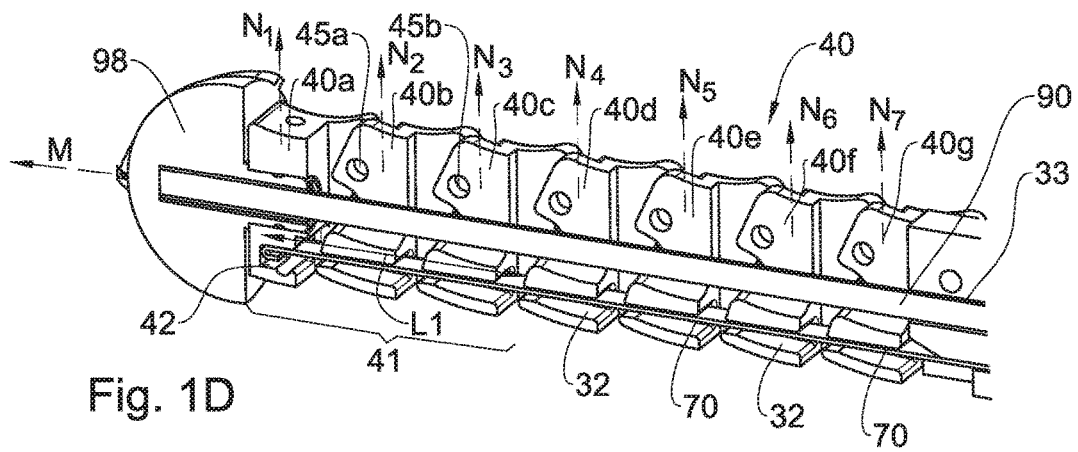
FIG. 1D is an enlarged view of section $A_1$ of FIG. 1C.
Figure 1E:
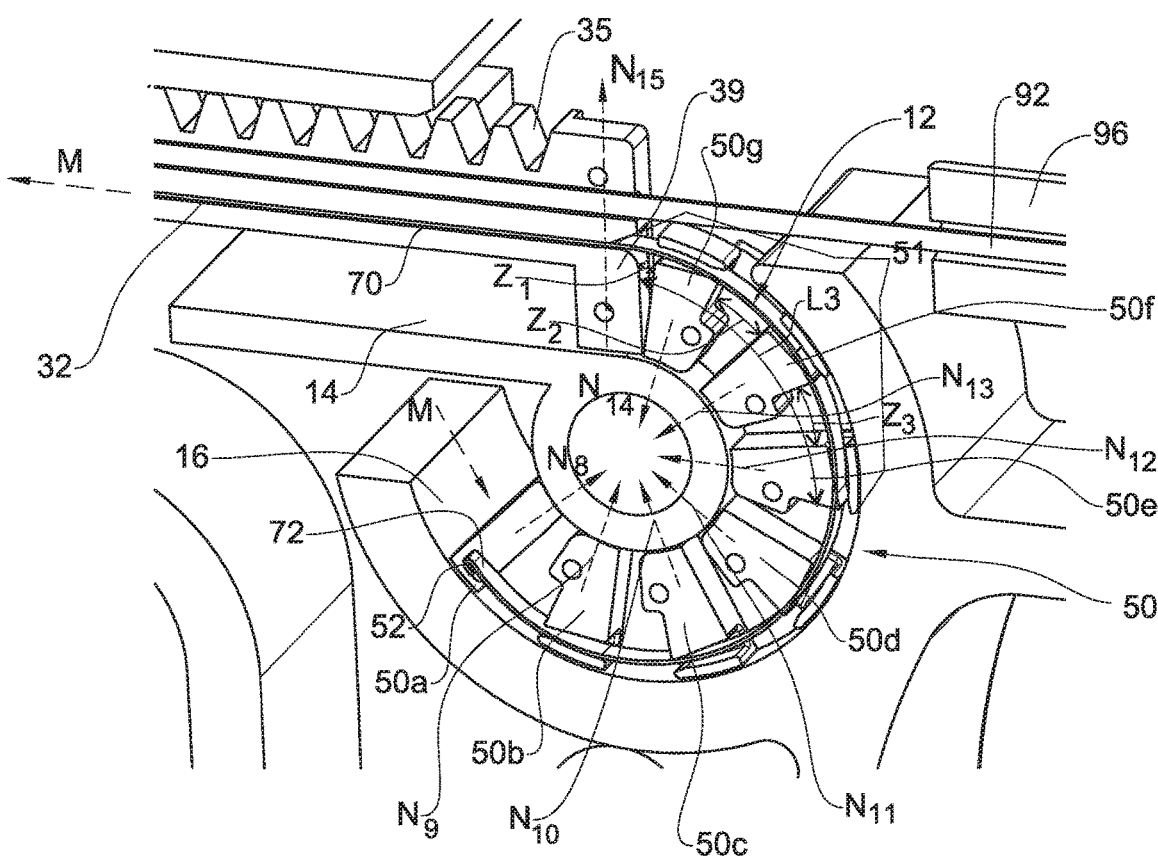
FIG. 1E is an enlarged view of section $A_2$ of FIG. 1C.
Figure 1F:
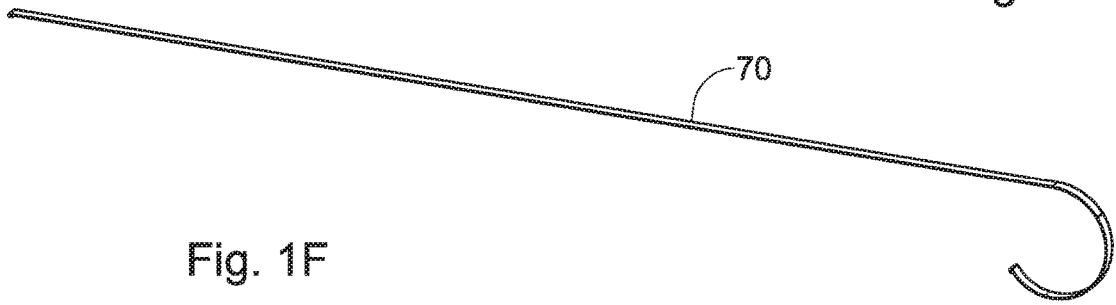
FIG. 1F is a side view of the deflecting member of FIG. 1C.
Figure 2A:
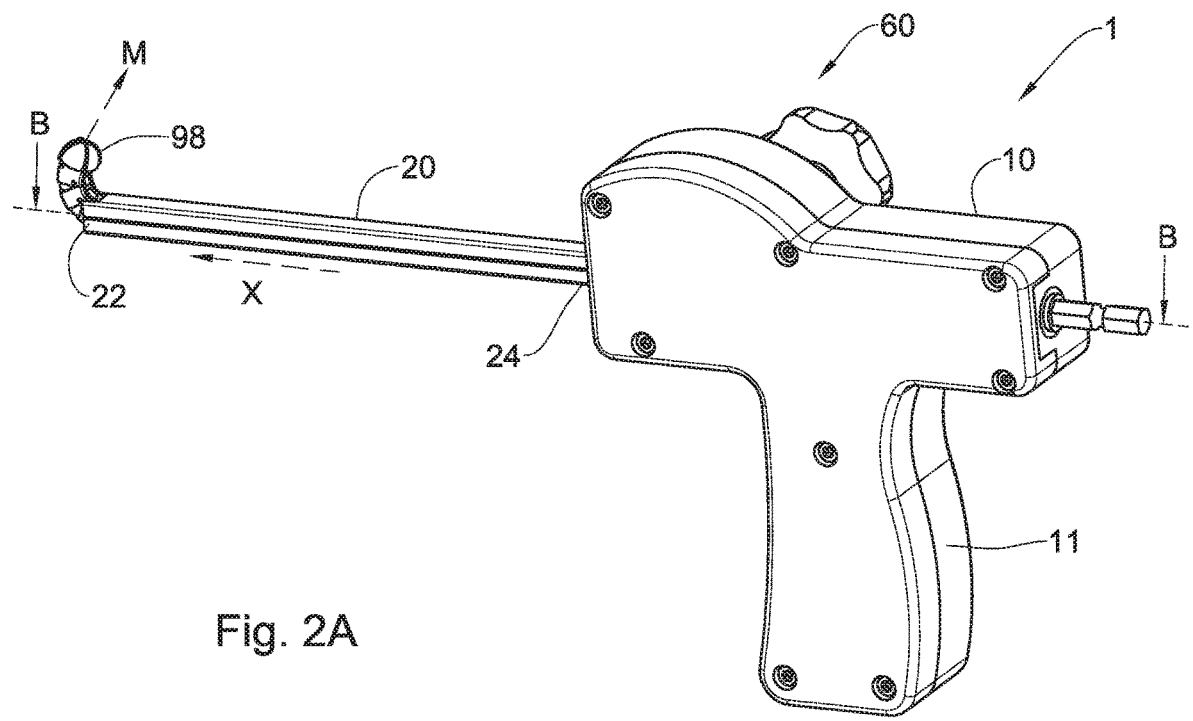
FIG. 2A is a side view of the apparatus of FIG. 1A, with its segmented assembly in its curved configuration.
Figure 2B:
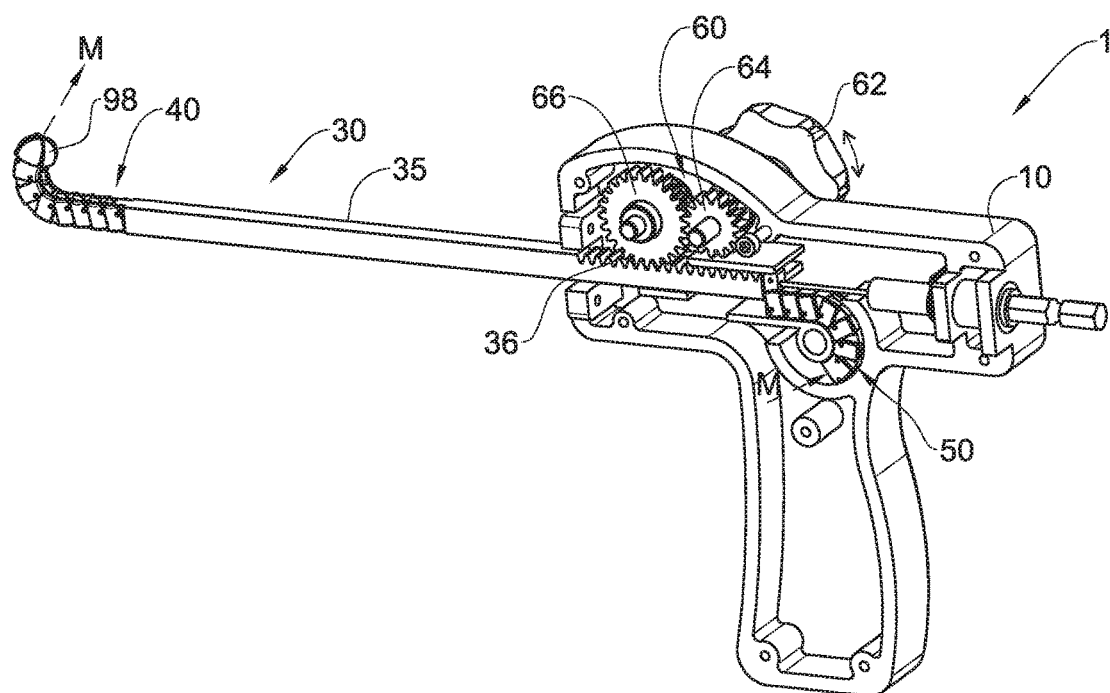
FIG. 2B is the apparatus of FIG. 2A with a part of its housing and its conduit removed.
Figure 2C:
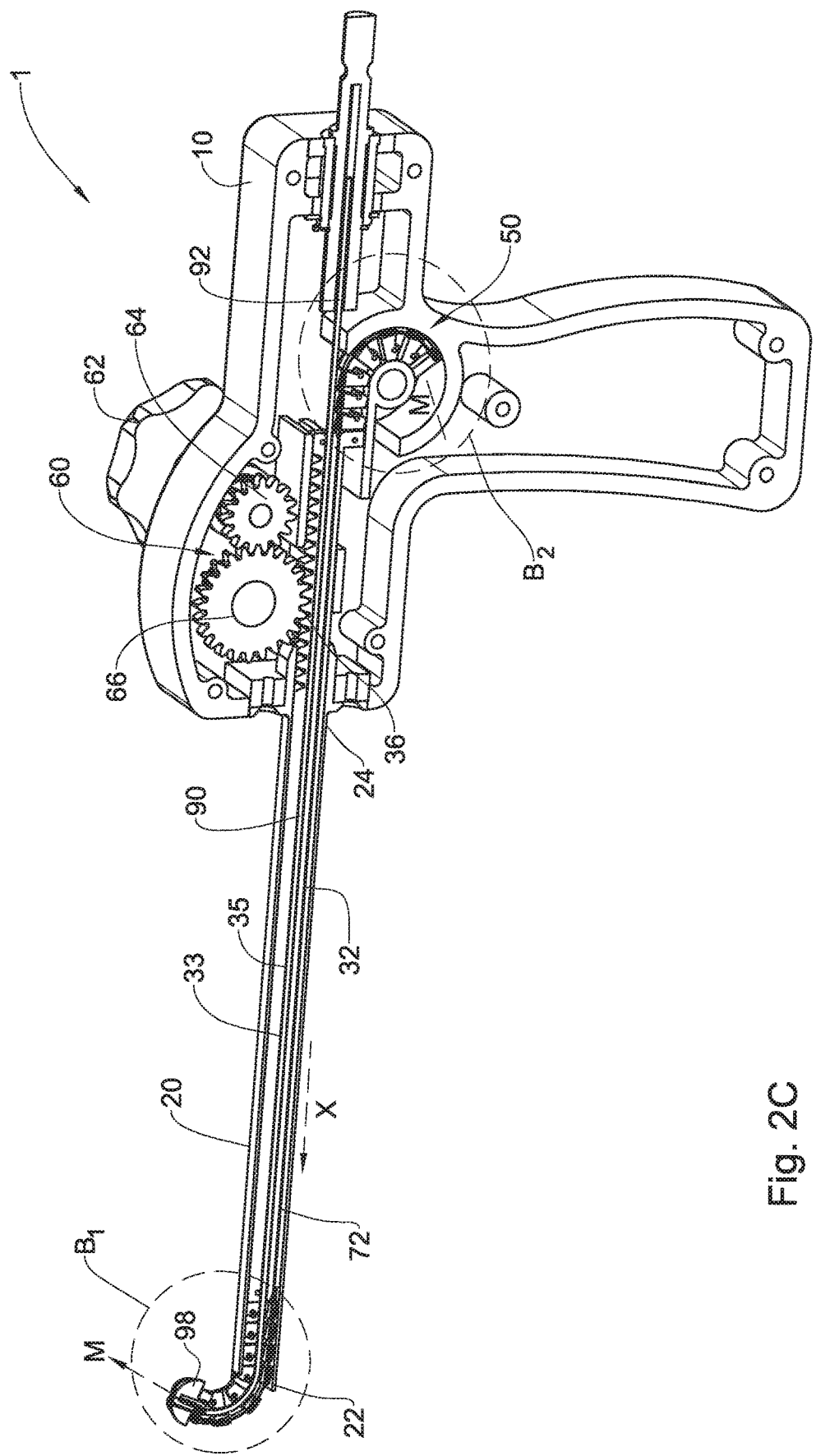
FIG. 2C is a cross-section view along line B-B in FIG. 2A.

FIG. 1F illustrates the shape of the deflecting member 70 in the position of FIGS. 1A-1E, and FIG. 2F illustrates the shape of the deflecting member 70 in the position of FIGS. 2A-2E. It can be seen from these figures that the shape of the deflecting member 70 corresponds to the shape of the elongated member 30.

Figure 3A:
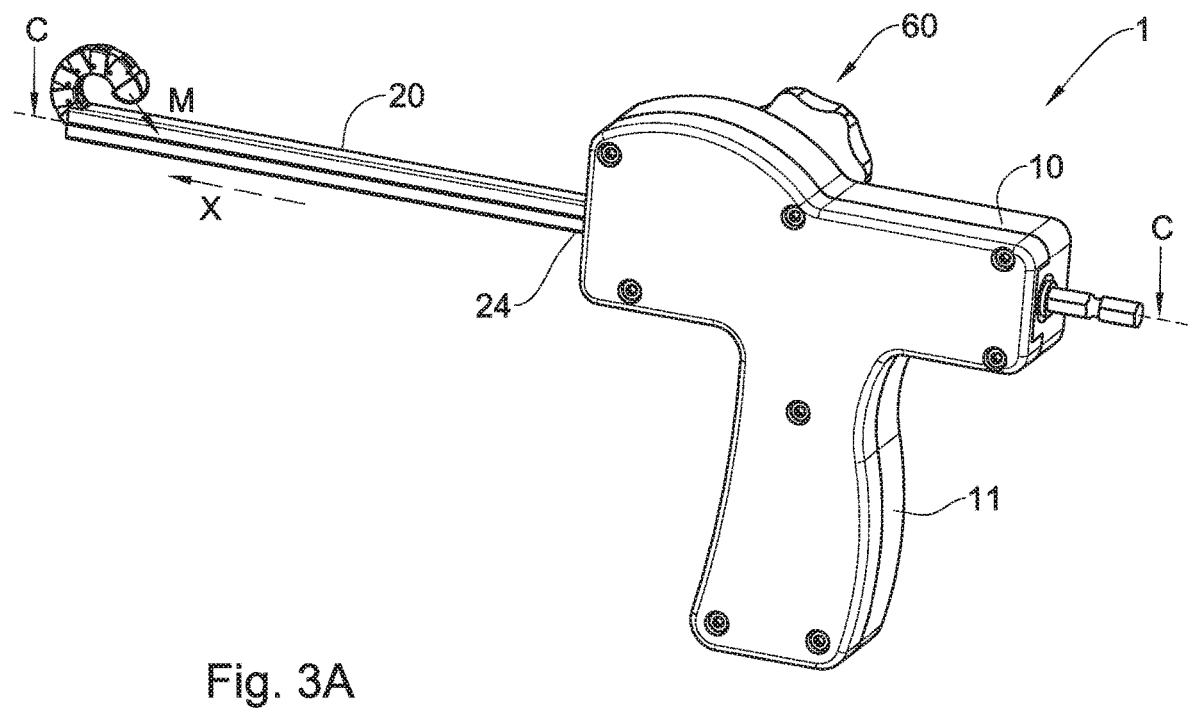
FIG. 3A is a side isometric view of the apparatus of FIG. 1A, with its segmented assembly in its curved configuration while the segmented assembly is advanced to extend from the conduit of the apparatus to an extent greater than the extent shown in FIG. 2A.
Figure 3B:
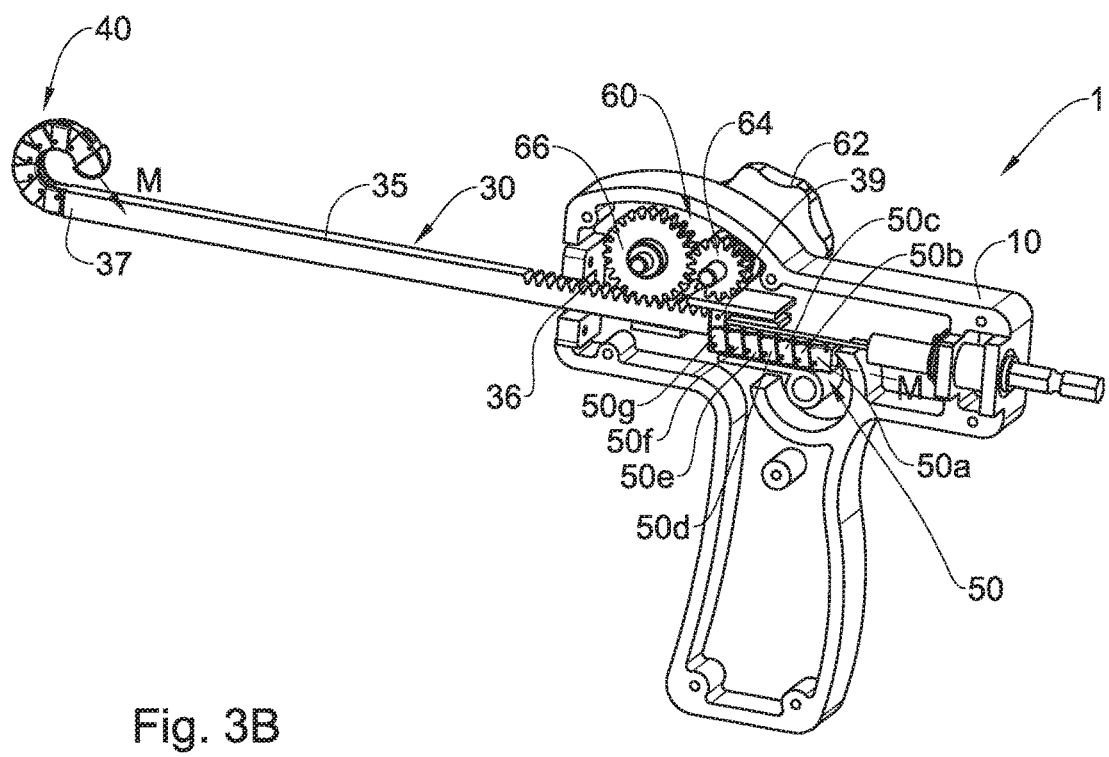
FIG. 3B is the apparatus of FIG. 3A with a part of its housing and its conduit removed.
Figure 3C:
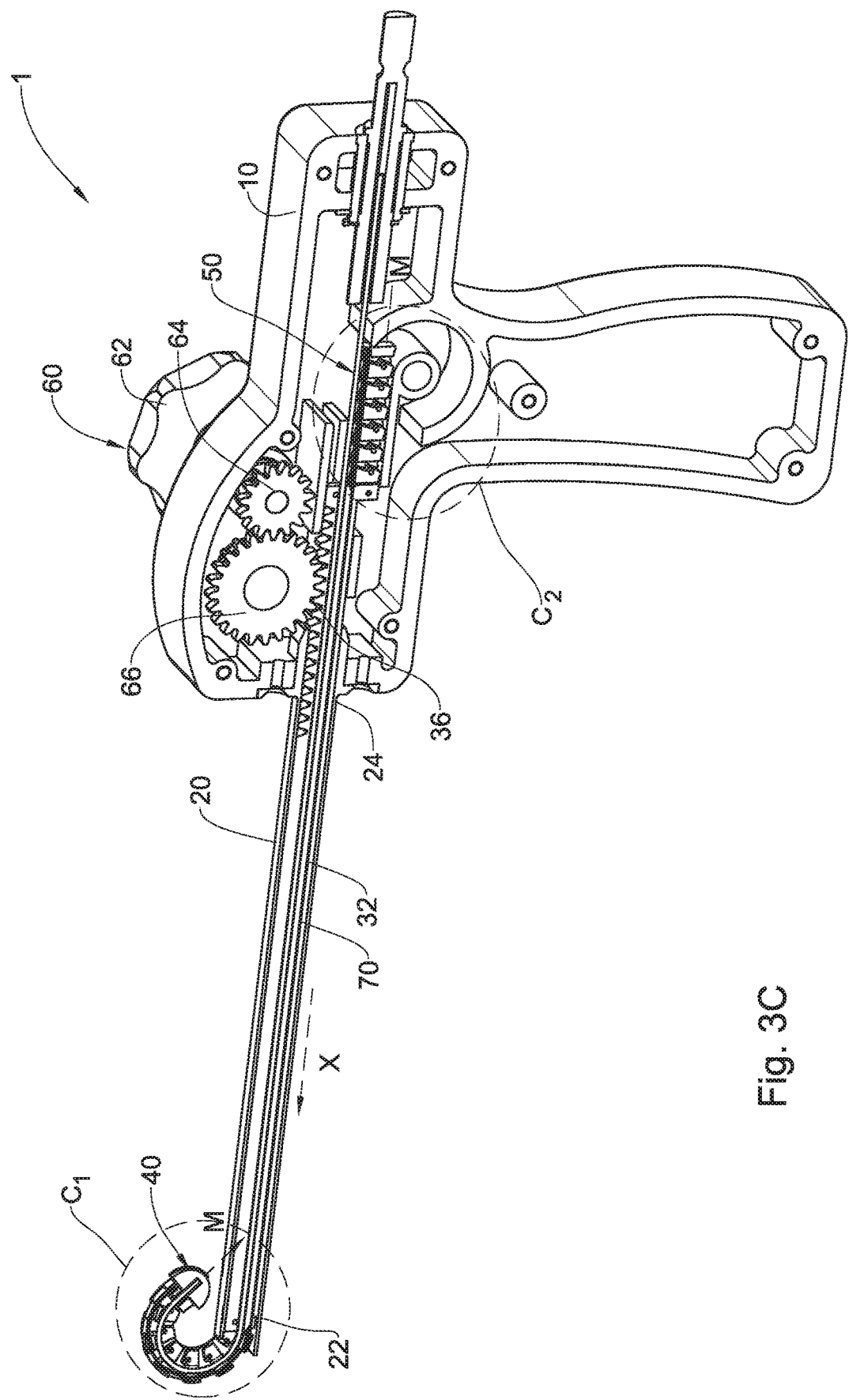
FIG. 3C is a cross-section view along line C-C in FIG. 3A.
Figure 3D:
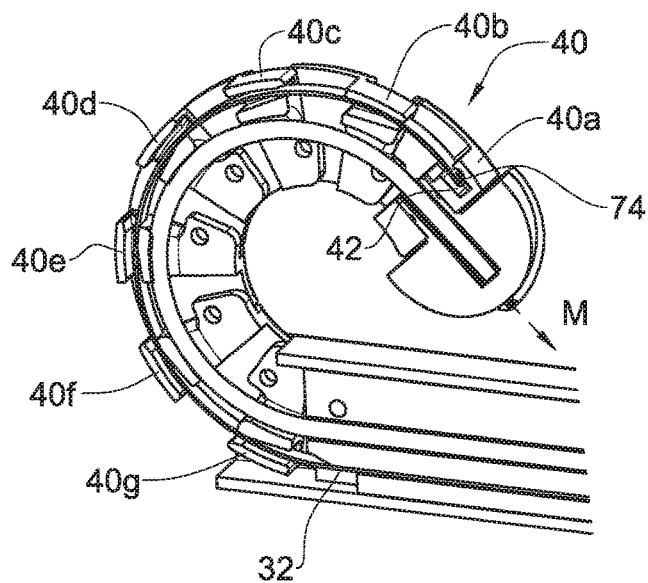
FIG. 3D is an enlarged view of section $C_1$ of FIG. 3C.
Figure 3E:
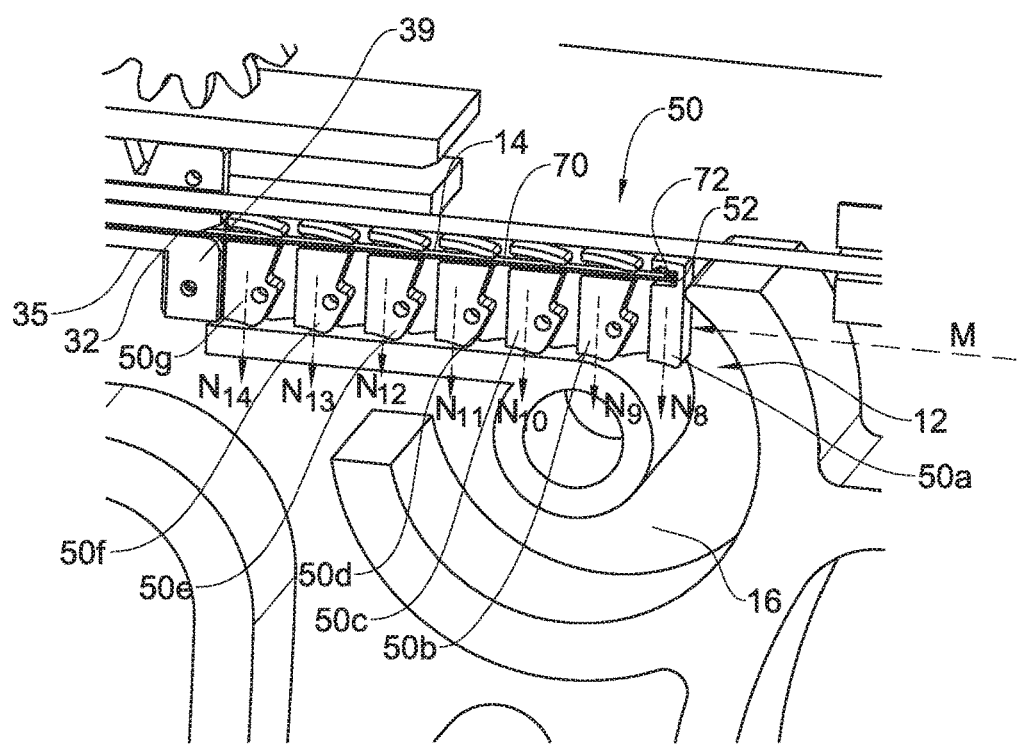
FIG. 3E is an enlarged view of section $C_2$ of FIG. 3C.
Figure 3F:
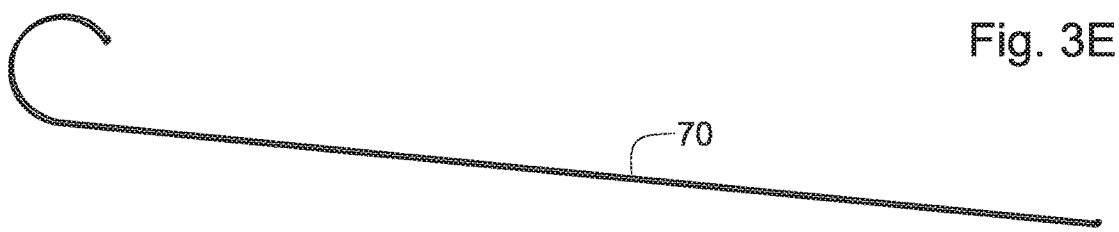
FIG. 3F is a side view of the deflecting member of FIG. 3C.

Further rotation of the handle 62 from the position of FIGS. 2A to 2F, can cause the segmented assembly 40 to extend from the conduit distal end 62 to a maximal extent as shown in FIGS. 3A to 3E, and the additional segmented assembly 50 to assume its additional straight configuration as clearly shown in FIGS. 3C and 3E. According to the above explanation, it is now clear how the additional segmented assembly 50 plays a role of an actuator.

It is appreciated that rotation of the handle 62 to an opposite direction will cause the elongated member 30 and the deflecting member 70 to move in the opposite direction. As a result of this rotation, the segmented assembly 40 and the additional segmented assembly 50 switch roles. Now, the most distal segment 40a is the one that exerts a pushing force of the deflecting member 70, causing a respective part of the additional segmented assembly 50 to assume its curved shape. In this case, the segmented assembly plays the role of an actuator.

Reference is now made specifically to FIGS. 1A to 2E in order to describe the drilling functionality of the apparatus 1.

The elongated member 30 has a second channel 33 extending along the segmented assembly 40 and the movable member 35. The second channel 33 accommodates a rotatable bendable shaft 90 having a proximal end 92 and a distal end 94. The proximal end 92 of shaft 90 is received within a rotating element 96 and the distal end 94 is mounted to a rotatable tip 98. The rotating element 96 is configured to be rotated manually or automatically by a motor (not shown), thereby causing rotation of the shaft 90, and respective rotation of the tip 98. The shaft 90 can be rotated in both the straight and the curved configurations of the segmented assembly 40. This allows providing a conventional straight drilling and drilling along a curved path by a single apparatus.

It is known in the field of drilling, that in order to effectively drill into an object, a pushing force should be applied by an operator on the drill during its operation. This pushing force advances the tip of the drill into the object.

Reference is now made to FIG. 1A, in order to describe the pushing forces applied on the apparatus 1 or components thereof during initiation of its drilling operation and change of configuration from the straight to the curved configuration.

A pushing force $F_1$ is exerted by the operator on the entire apparatus along the axis X in the direction of drilling;

A pushing force $F_2$ is exerted by the moving mechanism 60 on the elongated member 30 along the axis X; and A pushing force $F_3$ is exerted by the deflecting member 70 on the most distal segment 40a, having a vector component along the axis X.

In view of the above, the fact that the pushing forces $F_1$, $F_2$ and $F_3$ are exerted substantially in the same direction at least during initiation of the drilling operation, an effective drilling of the structure is obtained. When these forces are exerted, a superposition of them can provide an intensified and effective drilling within the object.

Reference is now made to FIGS. 2D and 4A to 4E which illustrate the segments of the elongated member 30 and in particular their structure. As can clearly be seen in the drawings, the segments of the segmented assembly 40 and the additional segments of the additional segmented assembly 50 have a similar structure, and therefore, the explanation below is made with respect to the segments of the segmented assembly 40, although it is also relevant for the additional segments of the additional segmented assembly 50.

The segmented assembly 40 when in its curved configuration has a concave side 44 and a convex side 46. The pivots (e.g., the pivots 45a and 45b) of the segmented assembly 40 are disposed closer to the concave side 44 than the deflecting member 70. In particular, the pivots are disposed in proximity to the concave side 44 and the deflecting member 70 is disposed in proximity to the convex side 46. This structure allows exerting a pushing force by the deflecting member 70 at the distal end of the segmented assembly, which is directed from the convex side 46 towards the concave side 44 and is initiated closer to the convex side 46. This force is schematically shown in FIG. 2D. This force is much more effective than if the segmented assembly 40 would have been curved by a pulling force applied on the most distal segment 40a and initiated closer to the concave side 44.

In FIG. 2D, it is shown that the curved shape of the part 41 of the segmented assembly 40 is an arc characterized by a center of curvature O facing the concave side 44 and a radius R defined between the main axis M and the center of curvature O. The pivots of the part 41 are equally spaced from the center of curvature O to a first distance D1 and the deflecting member 70 which extends along the first channel 32 is spaced from the center of curvature O to a second distance D2 and the following condition is fulfilled: D1<R<D2.

As shown in FIGS. 4B to 40E, each pair of the adjacent segments has stabilizing portions 80 configured to engage each other in both the straight and the curved configurations of the segmented assembly 40 so as to resist torsion of the adjacent segments with respect to each other. The stabilizing portions 80 are disposed closer to the convex side 46 than the concave side 44. The stabilizing portions 80 are constituted by a projecting portion 81 of one segment and a recessed portion 82 of its adjacent segment, configured to receive the projecting portion 81. Detailed explanation regarding the structure of the stabilizing portions 80 is provided below with respect to a single segment.

Figure 4C:
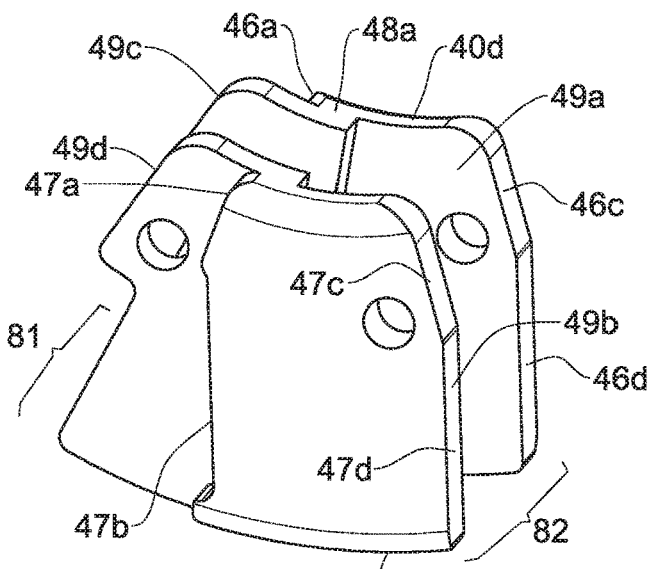
FIG. 4C is an enlarged view of a central segment of the three segments of FIG. 4B.
Figure 4D:
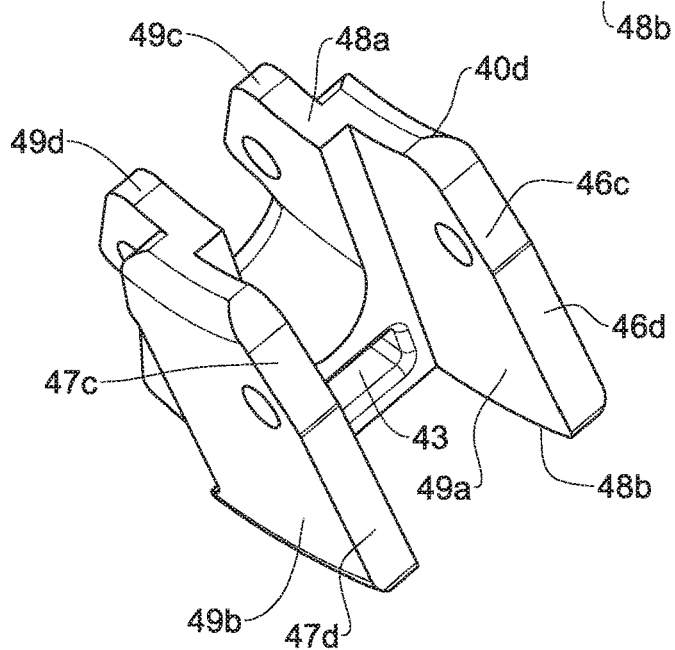
FIGS. 4D and 4E are other side views of the segment of FIG. 4C.
Figure 4E:
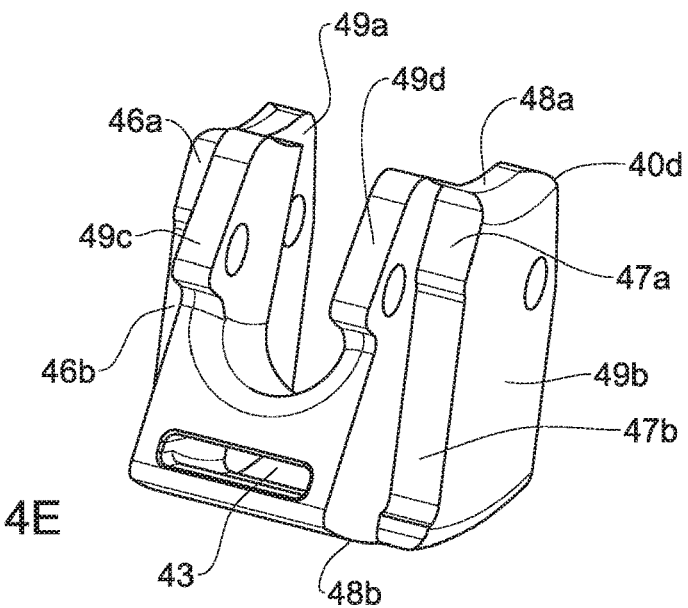

Reference is now made particularly to FIGS. 4C to 4E in which the segment 40d is shown from different points of view. The segment 40d has the following portions: an aperture 43 constituting a part of the second channel 33; an inner segment face 48a constituting a part of the concave side 44; an outer segment face 48b opposite thereto, constituting a part of the convex side 46; first and second opposite outer wings 49a and 49b, defining the recessed portion 82, respectively extending between the inner segment face 48a and the outer segment face 48b; and first and second opposite inner wings 49c and 49d, constituting the projecting portion 81, respectively extending between the inner segment face 48a and the outer segment face 48b. The first and second inner wings 49c and 49d of one segment are configured to be received and pivotally movable within the recessed portion 82 formed between the first and second outer wings 49a and 49b of its adjacent segment, thereby forming the segmented assembly and allowing the segmented assembly to change its configuration.

The connection between two adjacent segments is such that the first outer wing 49a of one segment is pivotally connected to the first inner wing 49c of its adjacent segment and the second outer wing 49b of said one segment is pivotally connected to the first inner wing 49d of the adjacent segment.

The first outer wing 49a comprises the following four surfaces: a first front contact surface 46a; a second front contact surface 46b; a first rear contact surface 46c and a second rear contact surface 46d. The second outer wing 49b comprises the following four surfaces: a first front contact surface 47a; a second front contact surface 47b; a first rear contact surface 47c and a second rear contact surface 47d.

In the straight configuration of the segmented assembly, the second rear contact surfaces 46d and 47d of one segment contact the second front contact surfaces 46b and 47b of its adjacent segment, thereby providing a contact surface between the two adjacent segments in addition to the hinges therebetween.

In the curved configuration, the first front contact surfaces 46a and 47b of one segment contact the first rear contact surfaces 46c and 47c of its adjacent segment, thereby delimiting the deflection of these segments with respect to each other to a predefined extent. The contact between segments of the part 41 allows also transferring the pushing force exerted on the most distal segment 40a to at least one of its successive segments for causing them to form an angle between orientation axes of the adjacent segments. The location of the first front contact surfaces 46a and 47b and the first rear contact surfaces 46c and 47c with respect to each other defines the angle between the orientation axes of two adjacent segments. For example, this location defines the value of the angles $\alpha_1$, $\alpha_2$ and $\alpha_3$.

When the moving mechanism 60 is actuated for exerting a pushing force on the elongated member 30 for causing the part 41 to extend beyond the conduit distal end 22, this force is transferred along the segmented assembly as follows:

i. in two segments with orientation axes parallel to each other, the force is transferred via the contact between the second front contact surfaces 46b and 47b of one segment with the second rear contact surfaces 46d and 47d of its adjacent segment. This transfer of force is performed in addition to its transfer via the hinges between the segments; and ii. in two segments with orientation axes forming an angle between each other, the force is transferred via the contact between the first front contact surfaces 46a and 47a of one segment with the first rear contact surfaces 46c and 47c of its adjacent segment. This transfer of force is performed in addition to its transfer via the hinges between the segments.

Figure 5:
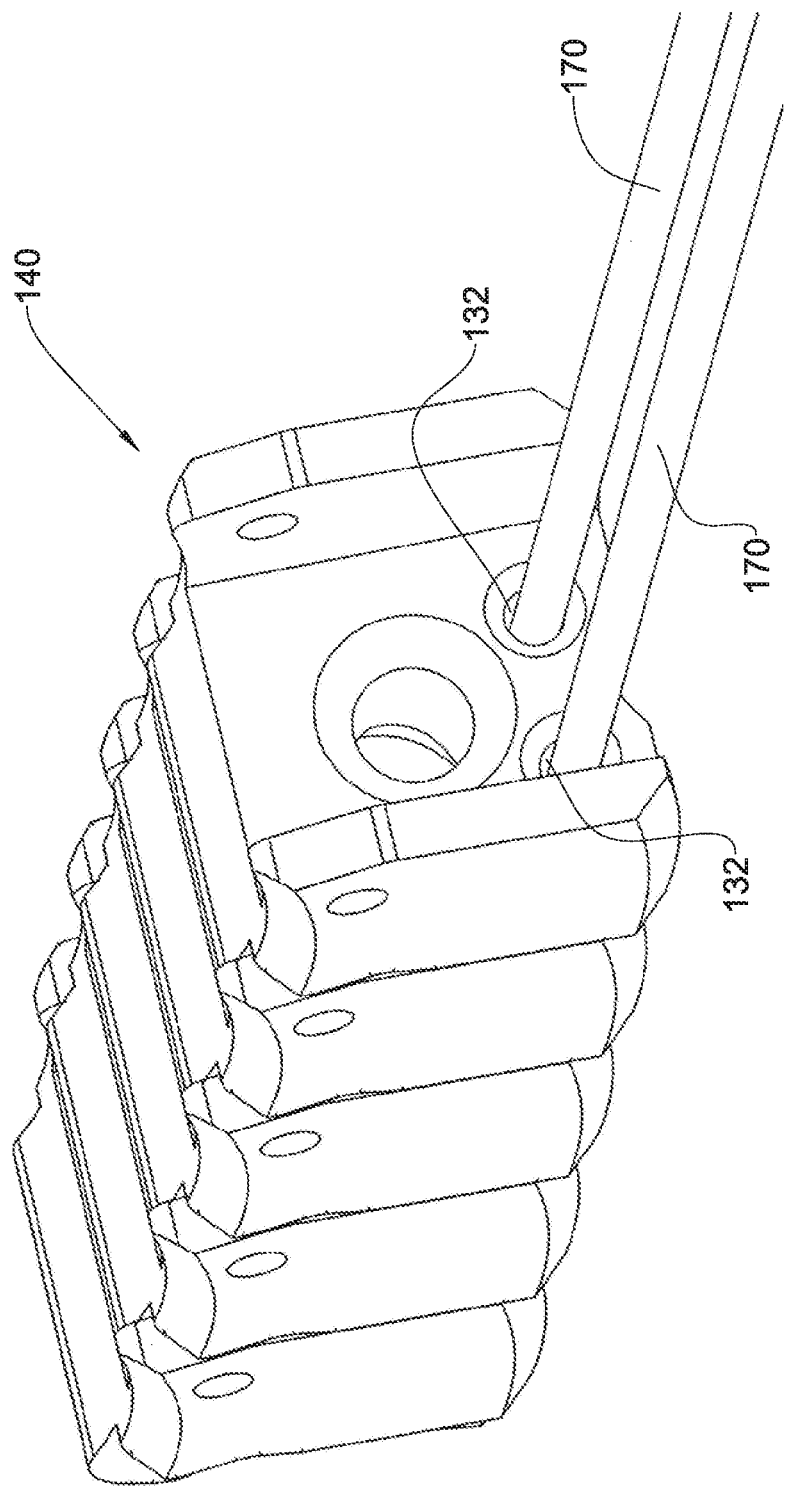
FIG. 5 is a side view of a segmented assembly with a deflecting member in the form of two bendable shafts, in accordance with another example of the presently disclosed subject matter.

Reference is now made to FIG. 5, in which another example of a segmented assembly 140 in accordance with the presently disclosed subject matter is shown. According to this example, the segmented assembly 140 has two first channels 132, each with a deflecting member 170. According to this example, the deflecting members 170 are elongated flexible and rigid shafts. The deflecting members 170 have functionality which is similar to that of the deflecting member 70.

Figure 6A:
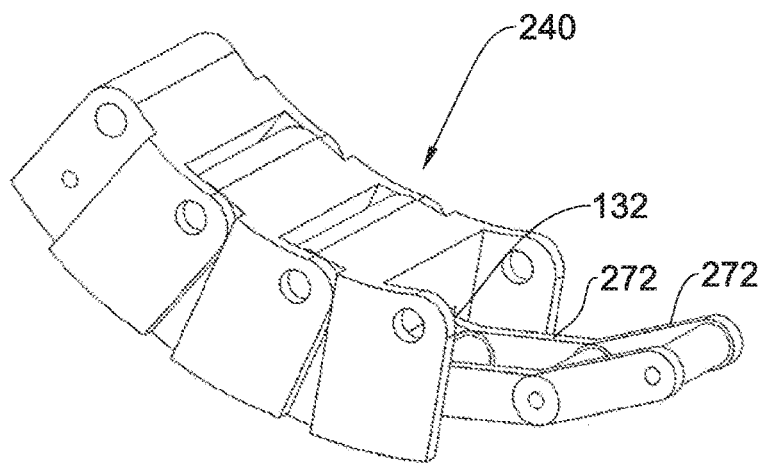
FIG. 6A is a side view of a segmented assembly in its curved configuration, in accordance with another example of the presently disclosed subject matter, with a deflecting member in the form of a roller chain.
Figure 6B:
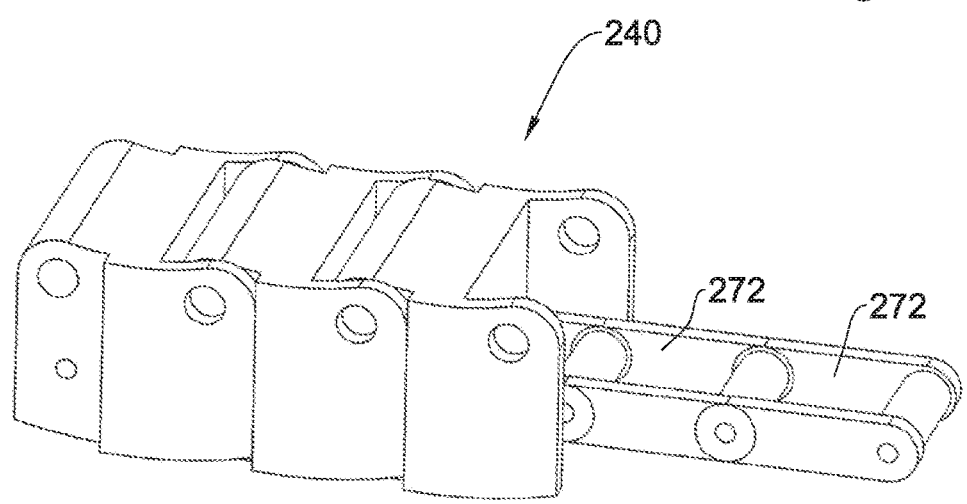
FIG. 6B is a side view of the segmented assembly of FIG. 6A in its straight configuration.
Figure 6C:
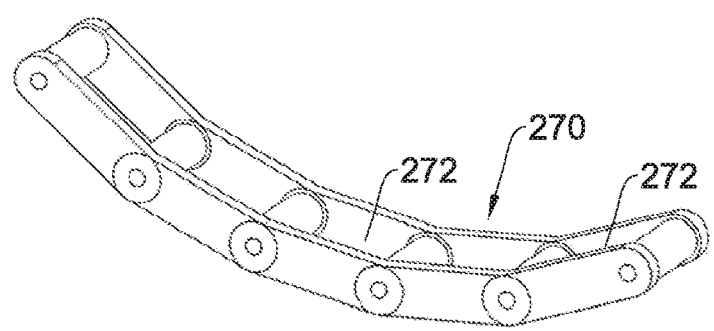
FIG. 6C is a side view of the roller chain of FIG. 6A.

Reference is now made to FIGS. 6A to 6C, in which another example of a segmented assembly 240 in accordance with the presently disclosed subject matter is shown. According to this example, the segmented assembly 240 has a channel 232 with a deflecting member 270 received therein. According to this example, the deflecting member 270 is a roller chain formed of a plurality of rigid segments 272 pivotally connected therebetween. The deflecting member 270 has functionally which is similar to that of the deflecting member 70. The difference between the deflecting members 70 and 270 is in that each of the segments 272 is non-bendable and thus is able to efficiently transfer pushing forces exerted therealong, and on the other the entire deflecting member 270 is able to be bent as required for deflecting the segmented assembly 240.

Figure 7A:
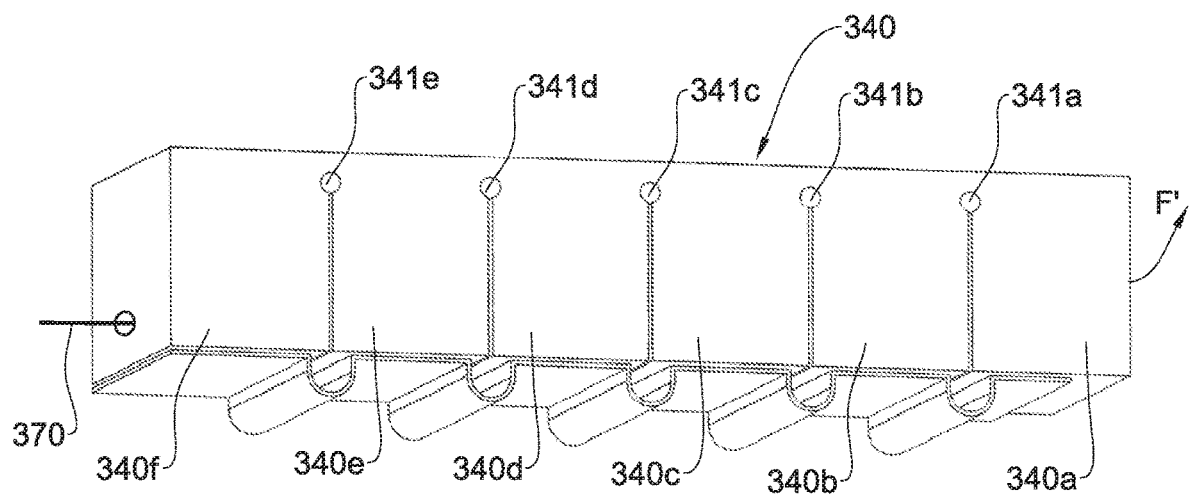
FIG. 7A is a side view of a part of a segmented assembly in its straight configuration, in accordance with another example of the presently disclosed subject matter.
Figure 7B:
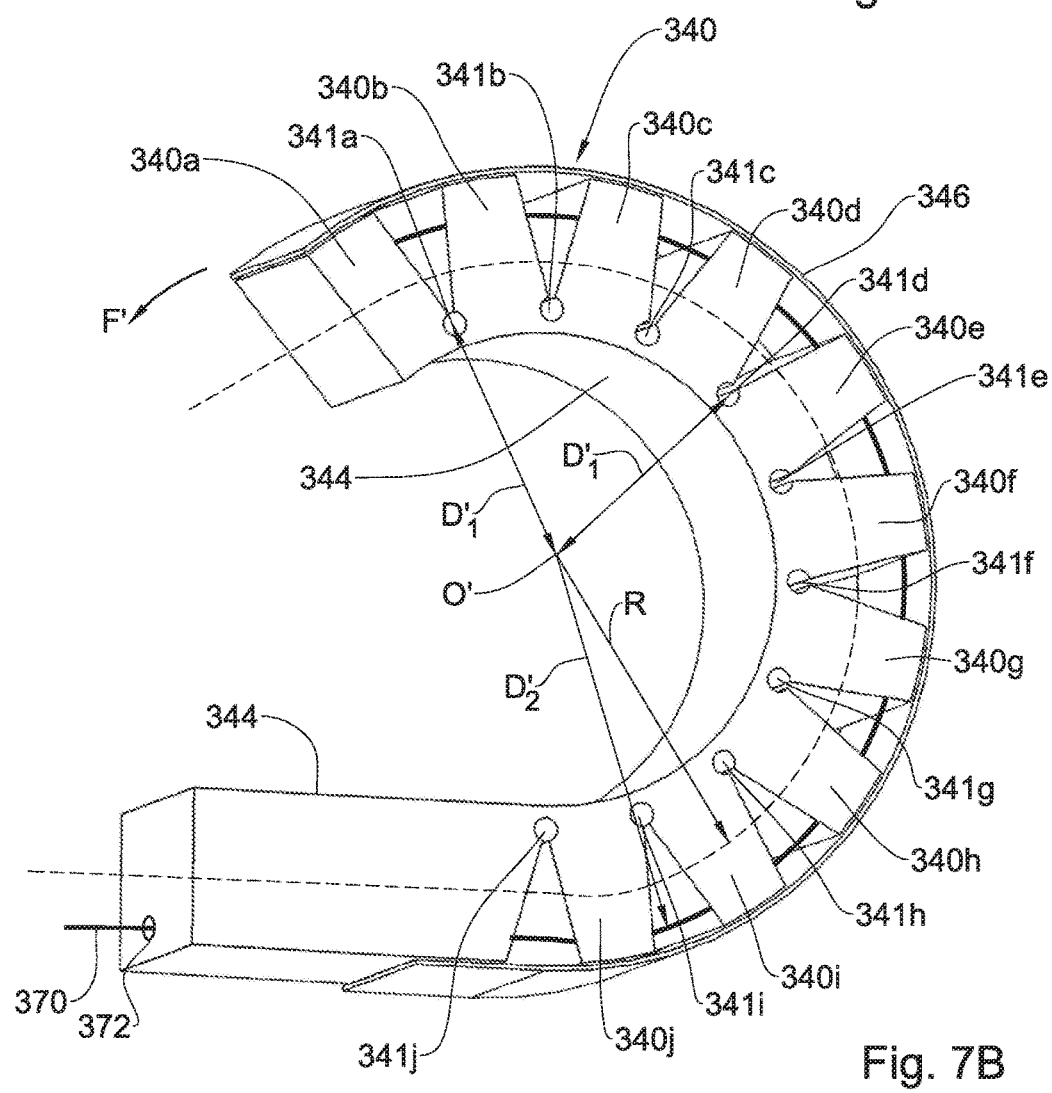
FIG. 7B is a side view of the segmented assembly of FIG. 7A in its curved configuration.

Reference is now made to FIGS. 7A and 7B, in which another example of a segmented assembly 340 in accordance with the presently disclosed subject matter is shown.

According to this example, the segmented assembly 340 is constructed of segments 340a-340j. The segments 340a-340j are hingedly connected to each other by effective hinges 341a-341j that are integrally formed as connecting portions of flexible material interconnecting between each pair of segments.

The segmented assembly 340 has a first channel 332 extending along a deflecting member 370. In FIG. 7A, the segmented assembly 340 is shown in its straight configuration, and in FIG. 7B, the segmented assembly 340 is shown in its curved configuration. The segmented assembly 340, when in its curved configuration has a concave side 344 and a convex side 346. The hinges 341a-341j of the segmented assembly 340 are disposed closer to the concave side 344 than the deflecting member 370. In particular, the hinges 341a-341j are disposed in proximity to the concave side 344 and the deflecting member 370 is disposed in proximity to the convex side 346. This structure allows exerting a pushing force F' by the deflecting member 370 at a most distal segment 340a, which is directed from the convex side 346 towards the concave side 344 and is initiated closer to the convex side 346. This force is much more effective than if the segmented assembly 340 would have been curved by a pulling force applied of the most distal segment 340a and initiated closer to the concave side 344.

In FIG. 7B, it is shown that the curved shape of the segmented assembly 340 is an arc characterized by a center of curvature O' facing the concave side 344 and a radius R' defined between a main axis M' of the segmented assembly 340 and the center of curvature O'. The hinges 341a-341j are equally spaced from the center of curvature O' to a first distance D1' and the deflecting member 370 extending along the first channel 332 is spaced from the center of curvature O' to a second distance D2' and the following condition is fulfilled: D1'<R'<D2'.

The segmented assembly 340 further has a strip 380 disposed at the convex side 346. The strip 380 connects two adjacent segments of the segmented assembly 340 so as to limit their rotatable movement with respect to each other to a predetermined extent.

Figure 8A:
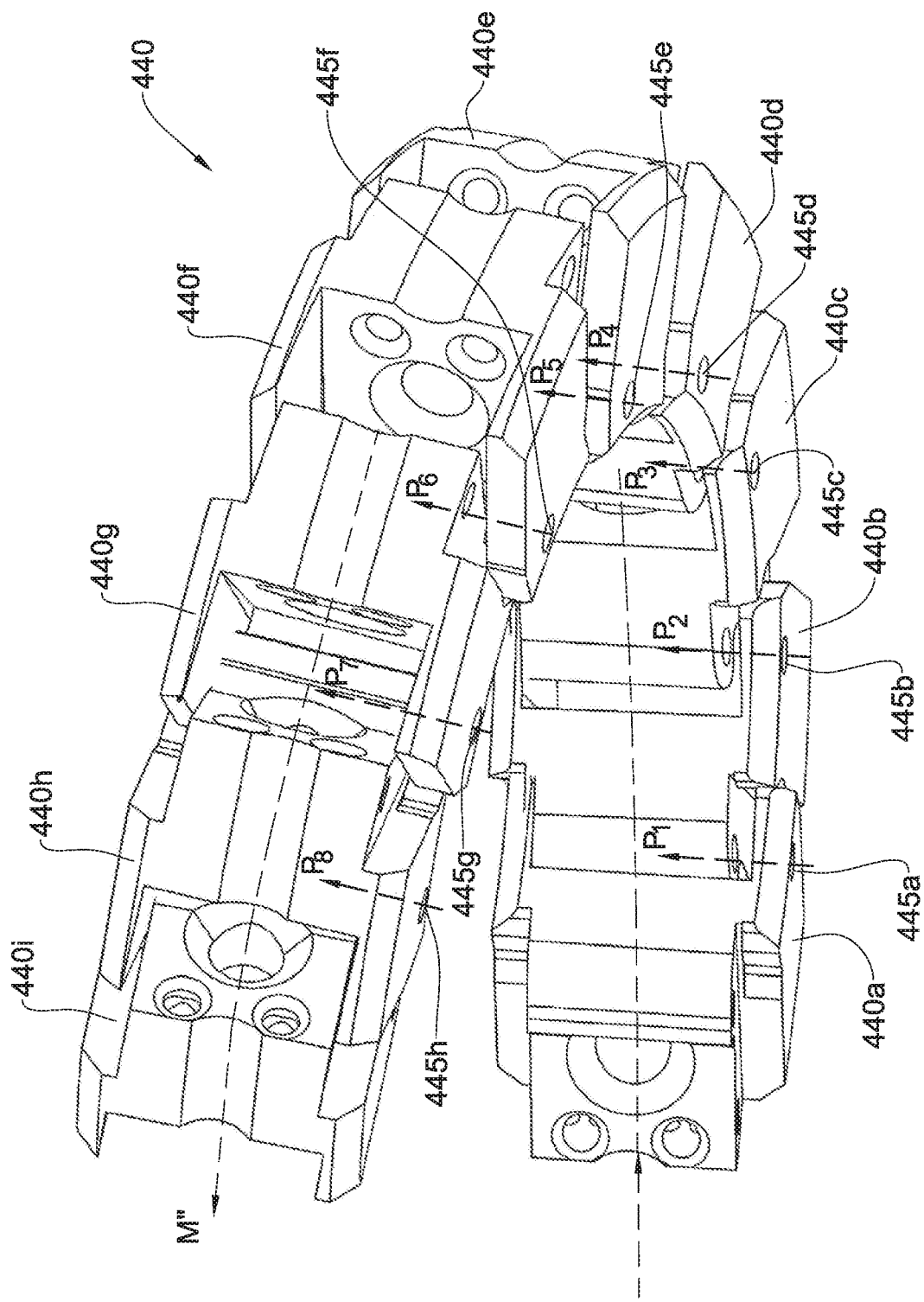
FIG. 8A is a side view of a segmented assembly, in accordance with another example of the presently disclosed subject matter, in which the segmented assembly is configured to assume a three dimensional helix shape.
Figure 8C:
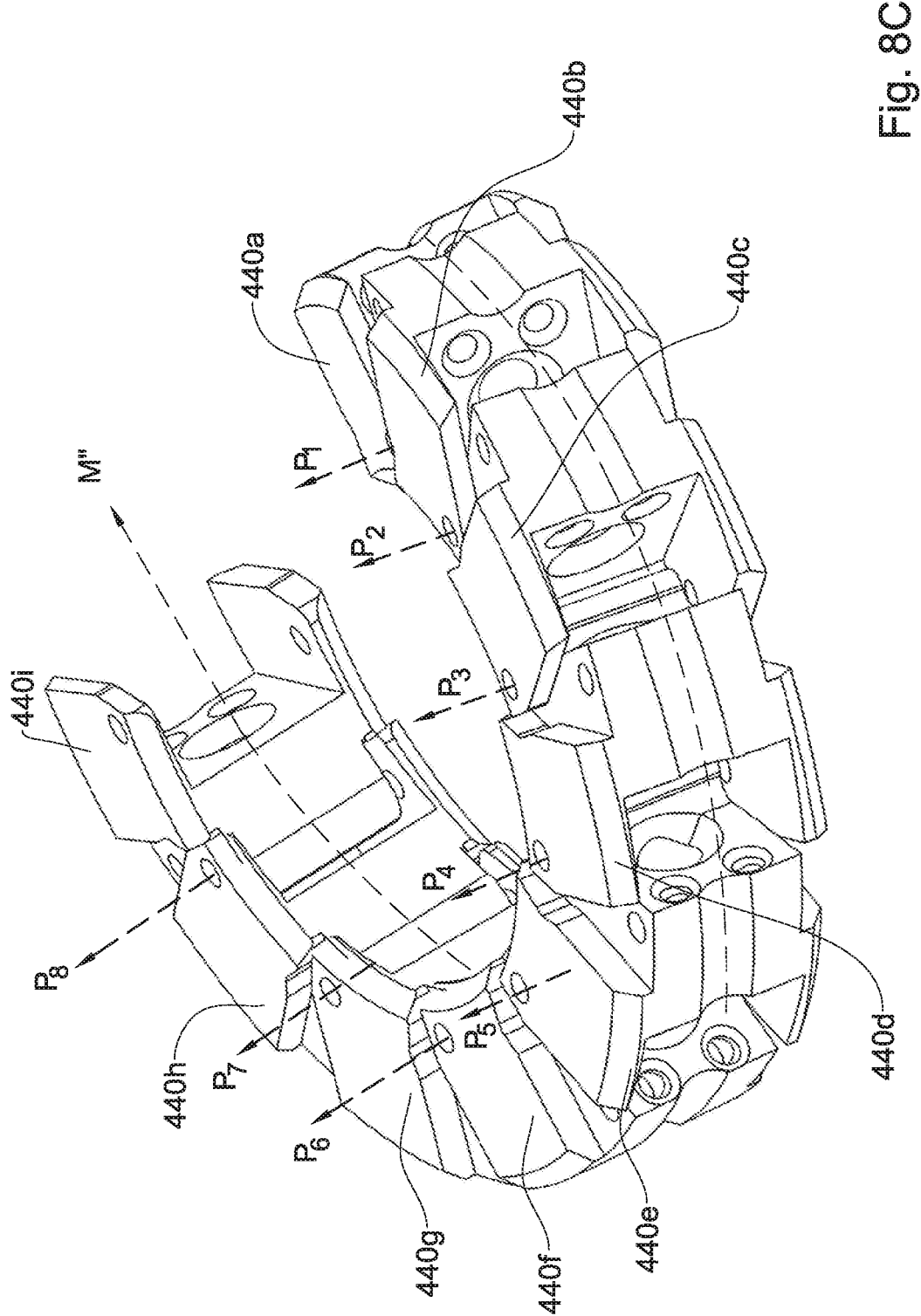
FIG. 8C is an additional view of the segmented assembly of FIG. 8A.

Reference is now made to FIG. 8A to 8C, in which a segmented assembly 440 is shown as a three dimensional helix.

The segmented assembly 440 has a longitudinal axis M'' main axis along which it extends. The segmented assembly 440 is formed of eight segments 440a, 440b, 440c, 440d, 440e, 440f, 440g, 440h and 440i that are pivotally connected to each other by respective pivots 445a, 445b, 445c, 445d, 445e, 445f, 445g and 445h. Each one of the pivots has a pivot axis $P_1$, $P_2$, $P_3$, $P_4$, $P_5$, $P_6$, $P_7$ and $P_8$. Each one of the pivots $P_1$-$P_8$ is angled with respect to the main axis M'' at obtuse angle which is slightly greater than 90 degrees). According to the present example, this angle is identical with respect to each one of the pivots $P_1$-$P_8$. The value of this angle defines the extension of the segmented assembly 440 along the main axis M'', and in particular, the spacing between the coils thereof.

The segmented assembly 440 of the above described helix shape can be used for lifting a part of the structure or for three dimensional advancement therein.

The invention claimed is:

1. An apparatus for advancement along a predetermined curved trajectory, comprising:
   a. a conduit having a conduit distal end;
   b. an elongated member having a main axis, at least partially extending within said conduit and movable therein along its length, said elongated member comprising a segmented assembly formed of a plurality of segments hingedly connected with each other, each having an orientation axis perpendicular to the main axis;

c. a deflecting member extending along said main axis so as to have a first state with a first extension along at least a part of the segmented assembly including its most distal segment, and a second state with a second extension along said part of the segmented assembly, the second extension exceeding the first extension;

d. a moving mechanism configured for applying a pushing force on the elongated member for moving the elongated member along the conduit and causing the part of the segmented assembly to extend beyond the conduit distal end and to be introduced into the conduit via the conduit distal end; and e. an actuator being mechanically associated with the deflecting member and configured for moving the deflecting member along said main axis and changing its state between the first and the second states, said deflecting member having a distal end mechanically associated at least with said most distal segment of said segmented assembly so as to allow said distal end to exert a pushing force on at least said most distal segment at least when the deflecting member changes its state from the first state to the second state;

said segmented assembly being configured to change its configuration, at least when said pushing force is exerted, from a straight configuration associated with said first state of the deflecting member, in which all the segments have their orientation axes parallel to each other, into a curved configuration associated with said second state of the deflecting member, in which at least said part of the segmented assembly extends beyond said conduit distal end and the corresponding segments of said pan change their orientation with respect to each other by means of their hinges so that the orientation axes of the corresponding segments form an angle therebetween, and so that said part of the assembly is rendered a curved shape;

said moving mechanism is mechanically associated with the actuator, so that operation of the moving mechanism to move the elongated member along the conduit entails operation of the actuator to move the deflecting member in the same direction, thereby assisting in the movement of the elongated member in that direction; and wherein the elongated member further comprises an additional segmented assembly and a movable member having a first end to which the segmented assembly is connected and a second end to which the additional segmented assembly is connected; said additional segmented assembly being formed of a plurality of additional segments hingedly connected with each other, each having an orientation axis perpendicular to the main axis; said deflecting member extending along said main axis so as to have an additional first state with an additional first extension along at least a part of the additional segmented assembly including its additional segment being most distal to the segmented assembly, and an additional second state with an additional second extension along said part of the additional segmented assembly; said additional first extension exceeding the additional second extension; said deflecting member having a proximal end mechanically associated at least with said most proximal segment of said additional segmented assembly so as to allow said most proximal segment to exert a pushing force on the proximal end at least when the deflecting member changes its state from the additional first state to the additional second state; the additional segmented assembly being configured to change its configuration, at least when said pushing force on the said proximal end is exerted, from an additional curved configuration associated with said additional first state of the deflecting member, in which all the additional segments are disposed in orientation with respect to each other by means of their hinges so that the orientation axes of the corresponding segments form an angle therebetween, into an additional straight configuration associated with said additional second state of the deflecting member, in which the segments of the part of the additional segmented assembly have their orientation axes parallel to each other.

2. The apparatus according to claim 1, wherein the actuator is constituted by the segmented assembly and by the additional segmented assembly so that:

operation of the moving mechanism to move the elongated member along the conduit to cause said segmented assembly to extend from the conduit distal end, entails the additional segmented assembly to change its configuration from the additional curved configuration to the additional straight configuration, which entails the most proximal segment of the additional segmented assembly to exert a pushing force of the proximal end on the deflecting member, causing it to move in the same direction and to change its state from the first to the second state, thereby changing the configuration of the segmented assembly from the straight to the curved configuration; and operation of the moving mechanism to move the elongated member along the conduit to cause said segmented assembly to be introduced into the conduit via the conduit distal end, entails the segmented assembly to change its configuration from the curved configuration to the straight configuration, which entails the most distal segment to exert a pushing force on the distal end of the deflecting member, causing it to move in the same direction and to change its state from the additional second state to the additional first state, thereby changing the configuration of the additional segmented assembly from the additional straight configuration to the additional curved configuration.

3. The apparatus according to claim 1, wherein the curved channel has a straight portion extending along the conduit for housing a part of the additional segmented assembly in its additional straight configuration and a curved portion for housing the part of the additional segmented assembly therein in the additional curved configuration, said additional segmented assembly being movable within the curved channel between its additional straight configuration and additional curved configuration.

4. An apparatus for advancement along a predetermined curved trajectory, comprising:

a. a conduit having a conduit distal end;

b. an elongated member having a main axis, at least partially extending within said conduit and movable therein along its length, said elongated member comprising a segmented assembly formed of a plurality of segments hingedly connected with each other, each having an orientation axis perpendicular to the main axis; and c. a deflecting member extending along said main axis so as to have a first state with a first extension along at least a part of the segmented assembly including its most distal segment, and a second state with a second extension along said part of the segmented assembly, the second extension exceeding the first extension;

said deflecting member having a distal end mechanically associated at least with said most distal segment of said segmented assembly so as to allow said distal end to exert a pushing force on at least said most distal segment at least when the deflecting member changes its state from the first state to the second state;

said segmented assembly being configured to change its configuration, at least when said pushing force is exerted, from a straight configuration associated with said first state of the deflecting member, in which all the segments have their orientation axes parallel to each other, into a curved configuration associated with said second state of the deflecting member, in which at least said part of the segmented assembly extends beyond said conduit distal end and the corresponding segments of said part change their orientation with respect to each other by means of their hinges so that the orientation axes of the corresponding segments form an angle therebetween, and so that said part of the assembly is rendered a curved shape, when in its curved configuration has a concave side and a convex side; at least in a majority of the segments, each pair of adjacent segments having stabilizing portions closer to the convex side than the concave side and being other than the hinged connection therebetween, said stabilizing portions being configured to engage each other in both the straight and the curved configurations of the segmented assembly so as to resist torsion of the adjacent segments with respect to each other.

5. The apparatus according to claim 4, wherein said stabilizing portions are constituted by a projecting portion of one segment and a recessed portion of its adjacent segment, configured to receive said projecting portion; wherein the hinges are disposed in proximity to the concave side and the deflecting member is disposed in proximity to the convex side; and wherein the curved shape is an arc characterized by a center of curvature O facing the concave side and a radius R defined between the main axis and the center of curvature O, the hinges of the part of the segmented assembly being equally spaced from said center of curvature O to a first distance D1 and the deflecting member extending along a first channel formed in the elongated member, said first channel being spaced from said center of curvature O to a second distance D2 and the following condition is fulfilled: D1<R<D2.

6. The apparatus according to claim 5, wherein each segment of at least a majority of said segments comprises: an inner segment face constituting a part of the concave side; an outer segment face opposite thereto, constituting a part of the convex side; first and second opposite outer wings, constituting at least a part of the recessed portion, respectively extending between the inner segment face and the outer segment face therebetween; and first and second opposite inner wings, constituting at least a part of the projecting portion, respectively extending between the inner segment face and the outer segment face; said first and second inner wings of one segment being received and hingedly movable within said recessed portion formed between said first and second outer wings of its adjacent segment, thereby forming said segmented assembly and allowing the segmented assembly to change its configuration.

7. The apparatus according to claim 6, wherein the connection between two adjacent segments is such that the first outer wing of one segment is pivotally connected to the first inner wing of its adjacent segment and the second outer wing of said one segment is pivotally connected to the first inner wing of the adjacent segment.

8. The apparatus according to claim 6, wherein each of the first and the second outer wings comprises: a first front contact surface; a second front contact surface; a first rear contact surface and a second rear contact surface, so that in the straight configuration, the second rear contact surfaces of one segment contact the second front contact surfaces of its adjacent segment, thereby providing a contact surface between the two adjacent segments in addition to the hinges therebetween, and in the curved configuration, the first front contact surfaces of one segment contact the first rear contact surfaces of its adjacent segment, thereby delimiting the deflection of these segments with respect to each other to a predefined extent and transferring the pushing force from the most distal segment to at least one of its successive segments for causing them to form an angle between orientation axes of the adjacent segments.

9. The apparatus according to claim 8, further comprising a moving mechanism configured for applying a pushing force on the elongated member for moving the elongated member along the conduit and causing the part of the segmented assembly to extend beyond the conduit distal end and to be introduced into the conduit via the conduit distal end, wherein exertion of the pushing force by the moving mechanism transfers this force between two segments disposed in the straight orientation with respect to each other by the contact between the second front contact surfaces of one segment with the second rear contact surfaces of its adjacent segment, in addition to the hinges therebetween, and between two segments with an angle between their orientation axes by contact between the first front contact surfaces of one segment with the first rear contact surfaces of its adjacent segment, in addition to the hinges therebetween.

* * * * *